(12) United States Patent
Sinclair et al.

(10) Patent No.: US 11,400,279 B2
(45) Date of Patent: Aug. 2, 2022

(54) METHOD AND SYSTEM FOR ASSESSING LARYNGEAL AND VAGUS NERVE INTEGRITY IN PATIENTS UNDER GENERAL ANESTHESIA

(71) Applicant: Icahn School of Medicine at Mount Sinai, New York, NY (US)

(72) Inventors: Catherine F. Sinclair, New York, NY (US); Sedat Ulkatan, New York, NY (US); Maria Jose Tellez Garbayo, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 202 days.

(21) Appl. No.: 16/472,720

(22) PCT Filed: Dec. 22, 2017

(86) PCT No.: PCT/US2017/068333
§ 371 (c)(1),
(2) Date: Jun. 21, 2019

(87) PCT Pub. No.: WO2018/119454
PCT Pub. Date: Jun. 28, 2018

(65) Prior Publication Data
US 2020/0179676 A1   Jun. 11, 2020

Related U.S. Application Data

(60) Provisional application No. 62/552,755, filed on Aug. 31, 2017, provisional application No. 62/438,862, filed on Dec. 23, 2016.

(51) Int. Cl.
| | | |
|---|---|---|
| A61N 1/05 | (2006.01) |
| A61N 1/36 | (2006.01) |
| A61B 5/24 | (2021.01) |

(52) U.S. Cl.
CPC .............. *A61N 1/0519* (2013.01); *A61B 5/24* (2021.01); *A61N 1/36053* (2013.01)

(58) Field of Classification Search
CPC .............. A61N 1/0519; A61N 1/36053; A61N 1/36132; A61B 5/24; A61B 5/0803;
(Continued)

(56) References Cited

U.S. PATENT DOCUMENTS

| 4,907,602 A * | 3/1990 | Sanders ............... A61N 1/3601 607/72 |
| 5,016,647 A | 5/1991 | Sanders |

(Continued)

FOREIGN PATENT DOCUMENTS

| JP | 03-182230 | 8/1991 |
| JP | 2016-512150 | 4/2016 |

OTHER PUBLICATIONS

Sinclair C. F. et al. A novel methodology for assessing laryngeal and vagus nerve integrity in patients under general anesthesia.Clinical Neurophysiology. Jul. 2017, vol. 128, Issue 7, pp. 1399-1405.
(Continued)

*Primary Examiner* — Amanda K Hulbert
*Assistant Examiner* — Natasha Patel
(74) *Attorney, Agent, or Firm* — Leason Ellis LLP

(57) ABSTRACT

The system and method of the present invention takes advantage of the laryngeal adductor reflex (LAR), previously thought to be repressed during general anesthesia, for CIONM without placement of an electrode on the vagus nerve.

47 Claims, 15 Drawing Sheets

(58) Field of Classification Search
CPC . A61B 2505/05; A61B 5/6853; A61B 5/4041; A61B 5/4836
See application file for complete search history.

(56) References Cited

U.S. PATENT DOCUMENTS

| | | | |
|---|---|---|---|
| 5,024,228 A | 6/1991 | Goldstone et al. | |
| 5,584,290 A * | 12/1996 | Brain | A61B 5/285 |
| | | | 128/207.15 |
| 6,213,960 B1 * | 4/2001 | Sherman | A61N 1/39044 |
| | | | 607/42 |
| 7,805,195 B2 | 9/2010 | Zealear | |
| 8,065,014 B2 | 11/2011 | Zealear | |
| 8,688,237 B2 | 4/2014 | Stanislaus et al. | |
| 8,886,280 B2 | 11/2014 | Kartush | |
| 2006/0254595 A1 * | 11/2006 | Rea | A61M 16/0488 |
| | | | 128/207.14 |
| 2010/0063376 A1 | 3/2010 | Kartush | |
| 2010/0249639 A1 * | 9/2010 | Bhatt | A61M 16/04 |
| | | | 600/546 |
| 2010/0317956 A1 * | 12/2010 | Kartush | A61B 5/6858 |
| | | | 600/380 |
| 2011/0093032 A1 * | 4/2011 | Boggs, II | A61N 1/3611 |
| | | | 607/42 |
| 2011/0125212 A1 * | 5/2011 | Tyler | A61N 1/3601 |
| | | | 607/42 |
| 2011/0245647 A1 | 10/2011 | Stanislaus et al. | |
| 2011/0270342 A1 | 11/2011 | Buschman et al. | |
| 2013/0172714 A1 | 7/2013 | Li et al. | |
| 2014/0148672 A1 | 5/2014 | Li | |
| 2016/0081591 A1 | 3/2016 | Lever et al. | |
| 2016/0151628 A1 | 6/2016 | Simon et al. | |
| 2018/0042524 A1 * | 2/2018 | Inman | A61B 5/1107 |
| 2019/0059812 A1 * | 2/2019 | McFarlin | A61B 5/4893 |

OTHER PUBLICATIONS

Rendolph G. W. et al. Electrophysiologic Recurrent Laryngeal Nerve Monitoring During Thyroid and Parathyroid Surgery: International Standards Guideline Statement. Laryngoscope. Jan. 2011, 121:S1-S16.

Henriquez V. M. et al. Laryngeal reflex responses are not modulated during human voice and respiratory tasks. J Physiol. Dec. 15, 2007, 585(Pt 3), pp. 779-789.

* cited by examiner

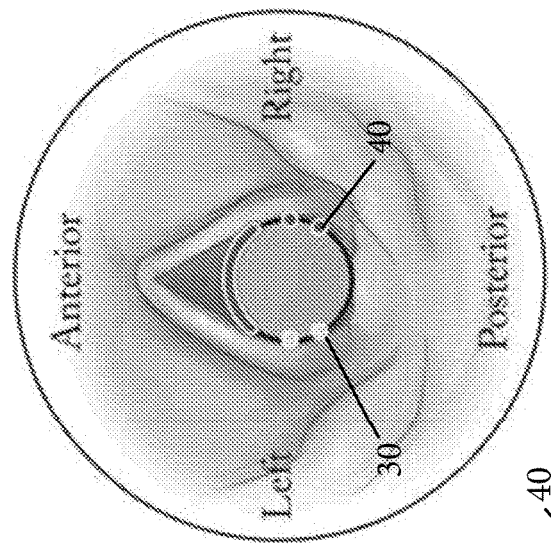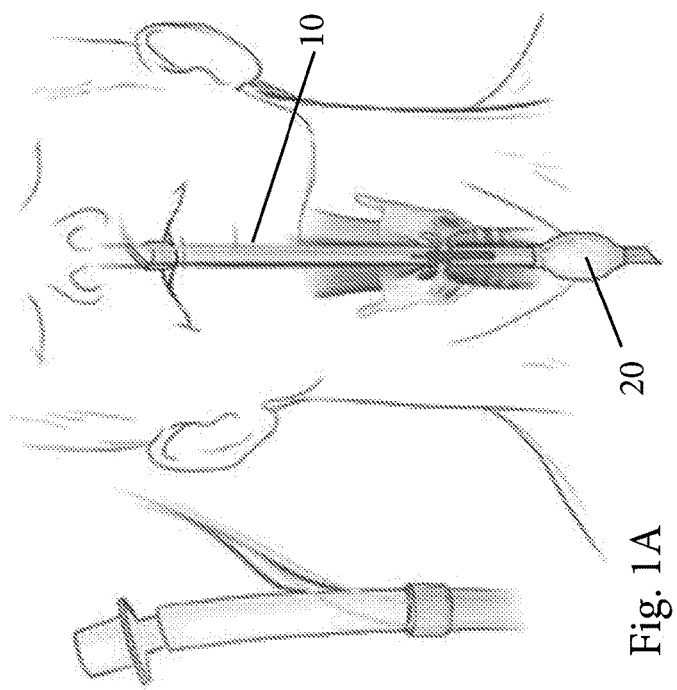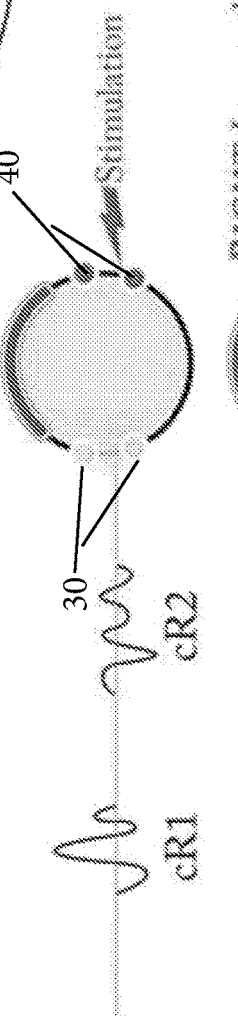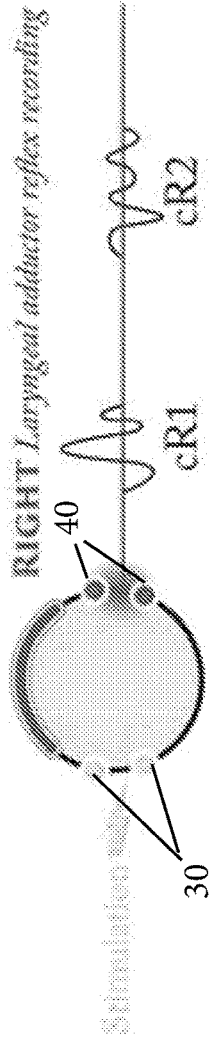
Fig. 1A
Fig. 1B
Fig. 1C

INTUBATION TUBE CROSS SECTIONS  IN-ABOVE AND BELOW THE RECORDING ELECTRODE

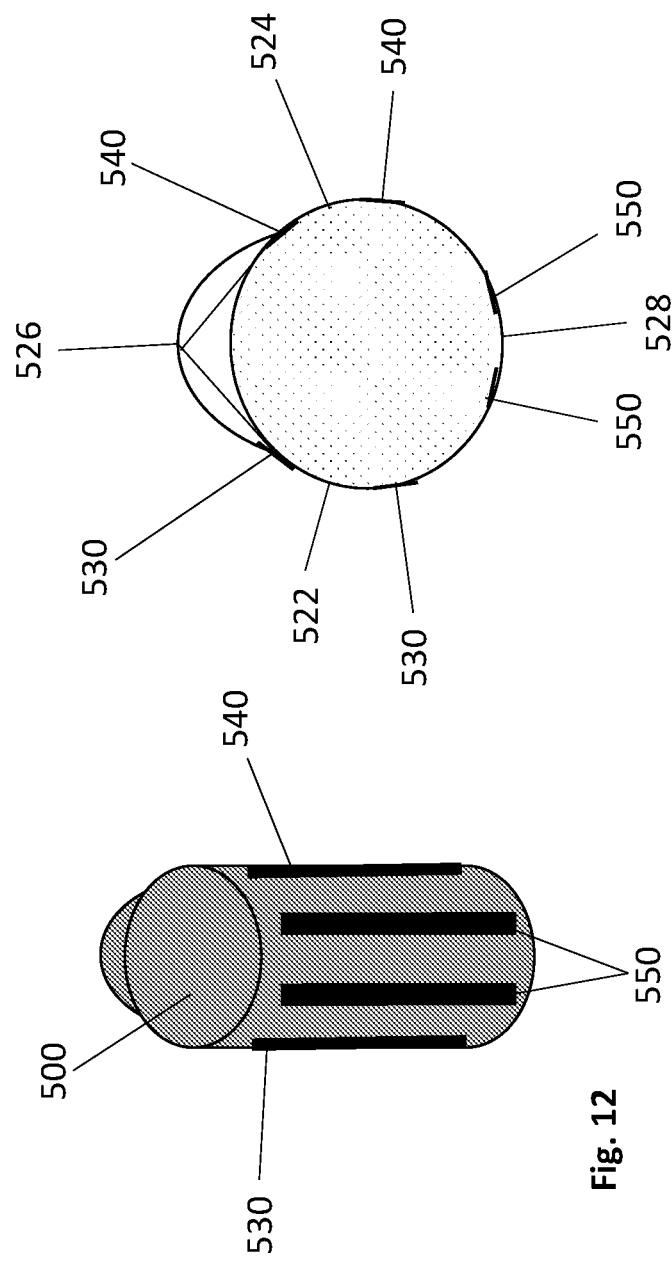

METHOD AND SYSTEM FOR ASSESSING LARYNGEAL AND VAGUS NERVE INTEGRITY IN PATIENTS UNDER GENERAL ANESTHESIA

CROSS-REFERENCE TO RELATED PATENT APPLICATIONS

This application is a U.S. National Phase Application under 35 U.S.C. § 371 of International Patent Application No. PCT./US2017/068333, filed Dec. 22, 2017, which is based on and claims priority to U.S. Provisional Patent Application 62/438,862, filed Dec. 23, 2016 and U.S. Provisional Patent Application 62/552,755, filed Aug. 31, 2017, each of which is incorporated by reference as if expressly set forth in their respective entirety herein.

TECHNICAL FIELD

The present invention is directed to a system and method for intraoperative neuro-monitoring of the laryngeal and vagus nerves and more specifically, relates to intraoperative neuro-monitoring of the laryngeal and vagus nerves by utilizing the laryngeal adductor response (reflex) (LAR).

BACKGROUND

The human larynx is one of the most complex organs in the body. It permits respiration and vocalization and protects the tracheobronchial tree from inhaled foreign objects.

The larynx has a complex neural supply from two different branches of the vagus nerve, the superior laryngeal nerve (SLN) and the recurrent laryngeal nerve (RLN). Afferent sensory input from the supraglottic and glottic larynx is carried in the internal branch of the superior laryngeal nerve (iSLN), with some overlap from the recurrent laryngeal nerve (RLN) at the glottis. The RLN is the predominant sensory nerve supply for the infraglottic region. The RLN provides the main motor innervation to laryngeal musculature, with the exception of the cricothyroid muscle which is supplied by the external branch of the SLN (eSLN). Monitoring of RLN, SLN and vagus nerve function is important during surgical procedures where these nerves may be at risk of injury. For thyroid and parathyroid surgeries, the RLN and eSLN lie within the operative field and there have been many recent guidelines endorsing the use of intra-operative neuromonitoring techniques to minimize post-operative neural complications. The most widely used monitoring technique for the RLN relies on endotracheal tube-based surface electrodes to measure compound muscle action potentials (CMAP) resulting from thyroarytenoid muscle contraction with vocal fold adduction. CMAPs are elicited either via direct RLN stimulation with a handheld neurostimulator probe or indirectly when the nerve is irritated by stretch, compression, etc.

More recently, intra-operative stimulation of the vagus nerve proximal to the exit point of the recurrent laryngeal nerve, either intermittently or continuously, has been advocated. In particular, several intra-operative neuromonitoring (IONM) strategies for the recurrent laryngeal nerve (RLN) exist to mitigate nerve damage during neck procedures, such as a thyroidectomy. These procedures utilize endotracheal tubes having electrodes disposed on an outer surface thereof. The IONM strategies may be intermittent (IIONM) or continuous (CIONM) in nature. For IIONM, identification of nerve malfunction occurs after the damage has taken place and thus, this strategy is less than ideal. CIONM requires a very difficult and risky surgical procedure in that it requires the opening of the carotid sheath and dissection between the internal jugular vein and the internal carotid artery to place a simulation electrode on the vagus nerve. Moreover, the electrode can easily dislodge.

The laryngeal adductor reflex (LAR) is an involuntary protective response triggered by sensory receptor stimulation in supraglottic (and glottic) mucosa. It will be understood that the term laryngeal adductor reflex and the term laryngeal adductor response are synonymous. Afferent nerve activity travels via the internal branch of the superior laryngeal nerve (iSLN) to the brainstem. The efferent pathway is via the vagus and recurrent laryngeal nerves, resulting in vocal fold adduction and thus tracheobronchial airway protection.

There is therefore a need for an alternative system and method for CIONM to prevent nerve injury during surgical procedures, such as neck surgery, and one which overcomes the above noted deficiencies associated with conventional IONM systems and methods.

SUMMARY

The system and method of the present invention takes advantage of the laryngeal adductor reflex (LAR), previously thought to be repressed during general anesthesia, for CIONM without placement of an electrode on the vagus nerve.

More specifically and according to the present disclosure, the laryngeal adductor reflex (LAR) is realized as a new monitoring method for laryngeal and vagus nerves. The present method relies on endotracheal tube electrodes for stimulating and recording laryngeal responses and the present method monitors the entire vagal reflex arc, including sensory, motor and brainstem pathways.

The LAR represents a novel method for intraoperatively monitoring laryngeal and vagus nerves. Advantages over current monitoring techniques include simplicity, ability to continuously monitor neural function without placement of additional neural probes and ability to assess integrity of both sensory and motor pathways. The LAR monitors the entire vagus nerve reflex arc and is thus applicable to all surgeries where vagal nerve integrity may be compromised.

According to one embodiment, an endotracheal tube for intraoperatively monitoring laryngeal and vagus nerves by eliciting laryngeal adductor response (LAR) in a patient that is under general anesthesia, that is of a type that preserves LAR, and by monitoring contralateral responses of the LAR that are detected after application of electrical stimulation. The endotracheal tube includes an endotracheal tube body having a first inflatable member and electrode area that has a generally triangular shaped cross-section configured for mating with a larynx anatomy of the patient. The electrode area includes a plurality of surface based recording electrodes and at least one stimulation electrode. The plurality of surface based electrodes includes at least one first surface based recording electrode that is located along a first side of the endotracheal tube and at least one second surface based recording electrode that is located along a second side the endotracheal tube. Each of the first and second surface based recording electrodes is configured to record contralateral responses of the LAR and the at least one stimulation electrode is configured to emit electrical stimulation.

The at least one stimulation electrode is located along a posterior side of the electrode area between the first side along which the at least one first surface based recording electrode is located and the second side along which the at least one second surface based recording electrode is located. In one embodiment, the at least one stimulation electrode comprises a pair of stimulation electrodes that are spaced apart and are parallel to one another. The at least one first surface based recording electrode comprises a pair of electrodes that are spaced apart and are parallel to one another and the at least one second surface based recording electrode comprises a pair of electrodes that are spaced apart and are parallel to one another. The pair of stimulation electrodes are located along the posterior of the endotracheal tube with the triangular shape being prominent along the anterior side of the endotracheal tube (i.e., the triangular shape points anteriorly). Placement of the stimulation electrodes within the electrode area along the posterior aspect of the tube enables bilateral CIONM.

In yet another aspect of the present invention, the LAR is used to define the topography of the larynx as it relates to elicitation of the laryngeal adductor reflex using electrical mucosal stimulation under general anesthesia.

In yet another aspect of the present invention, the LAR can alternatively be monitored by using the ipsilateral (iR1) component of the reflex for both stimulation and recording purposes. This monitoring is achieved using the endotracheal tubes with electrodes as described herein.

BRIEF DESCRIPTION OF THE DRAWING FIGURES

FIG. 1A is a schematic illustration of the methodology for eliciting the laryngeal adductor reflex by using an endotracheal tube containing bilaterally imbedded surface electrodes for stimulating and recording;

FIG. 1B is a schematic illustration showing a right pair of electrodes and a left pair of electrodes coming into direct contact with the right and left vocal folds, respectively;

FIG. 1C is a schematic illustration showing that the LAR is elicited by electrical stimulation of the laryngeal mucosa on the side contralateral to the operative field and electrodes ipsilateral to the surgical field (and contralateral to the stimulation side) are used to record the contralateral R1 and R2 responses;

Figure 7:
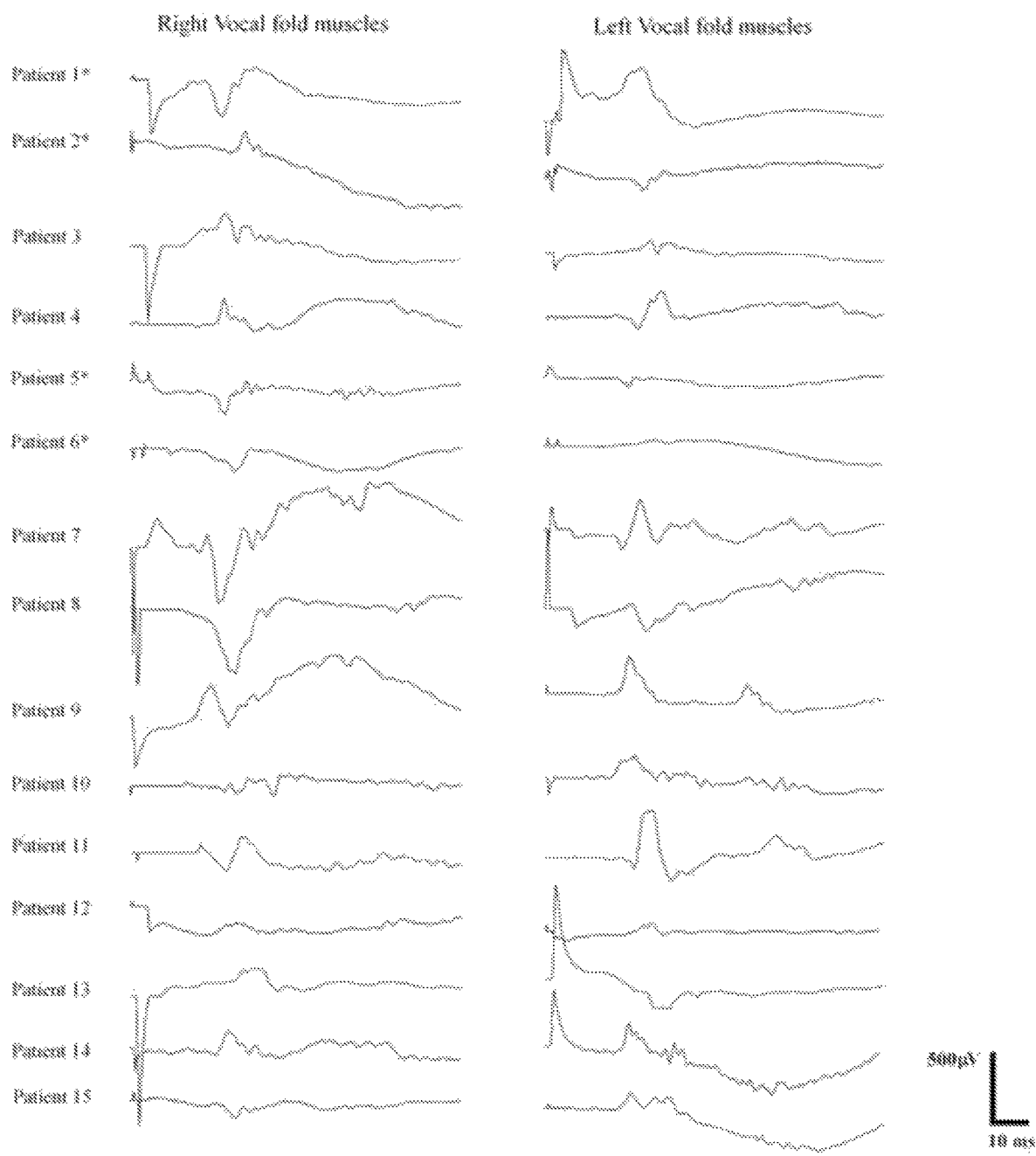
Figure 8:
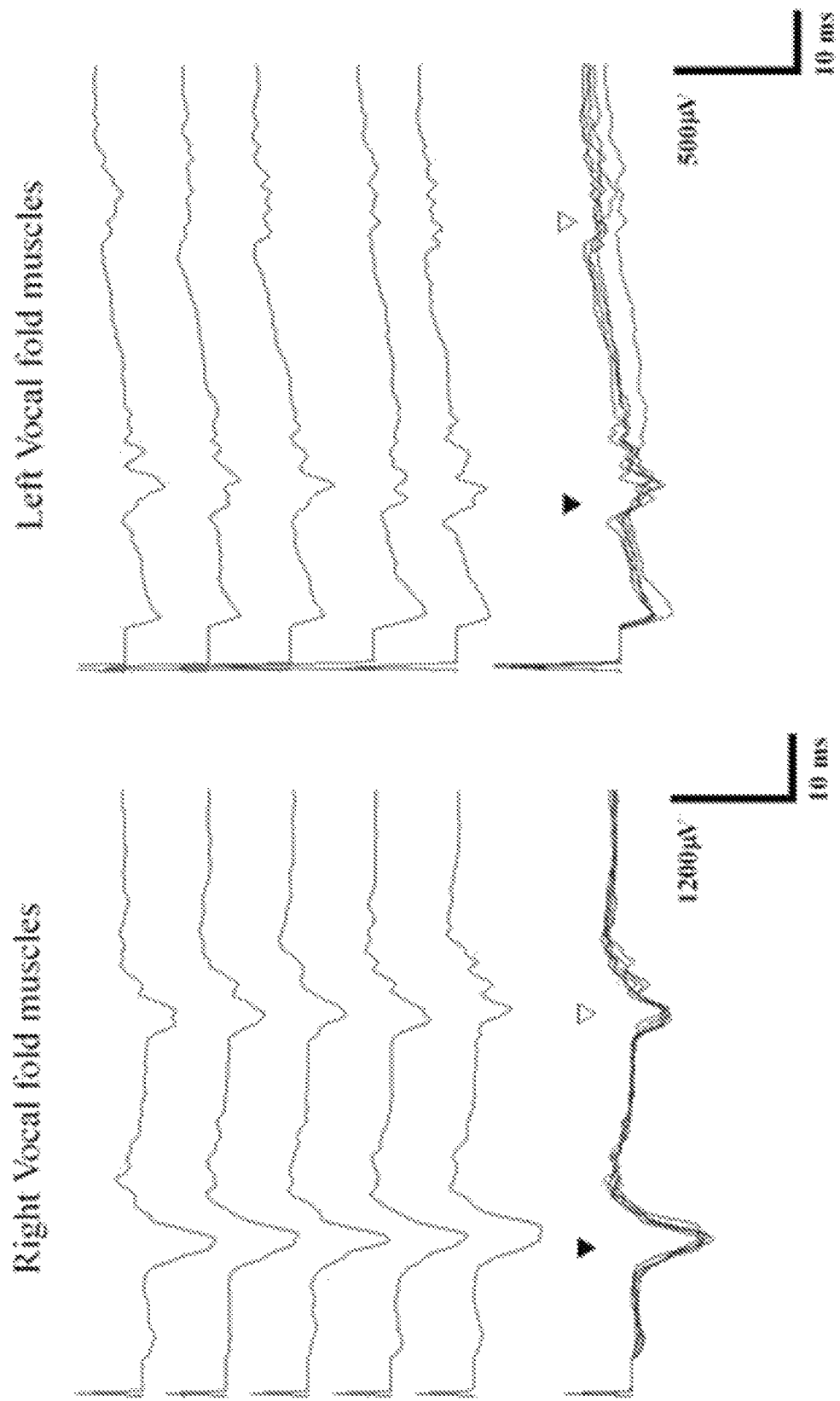
Figure 9:
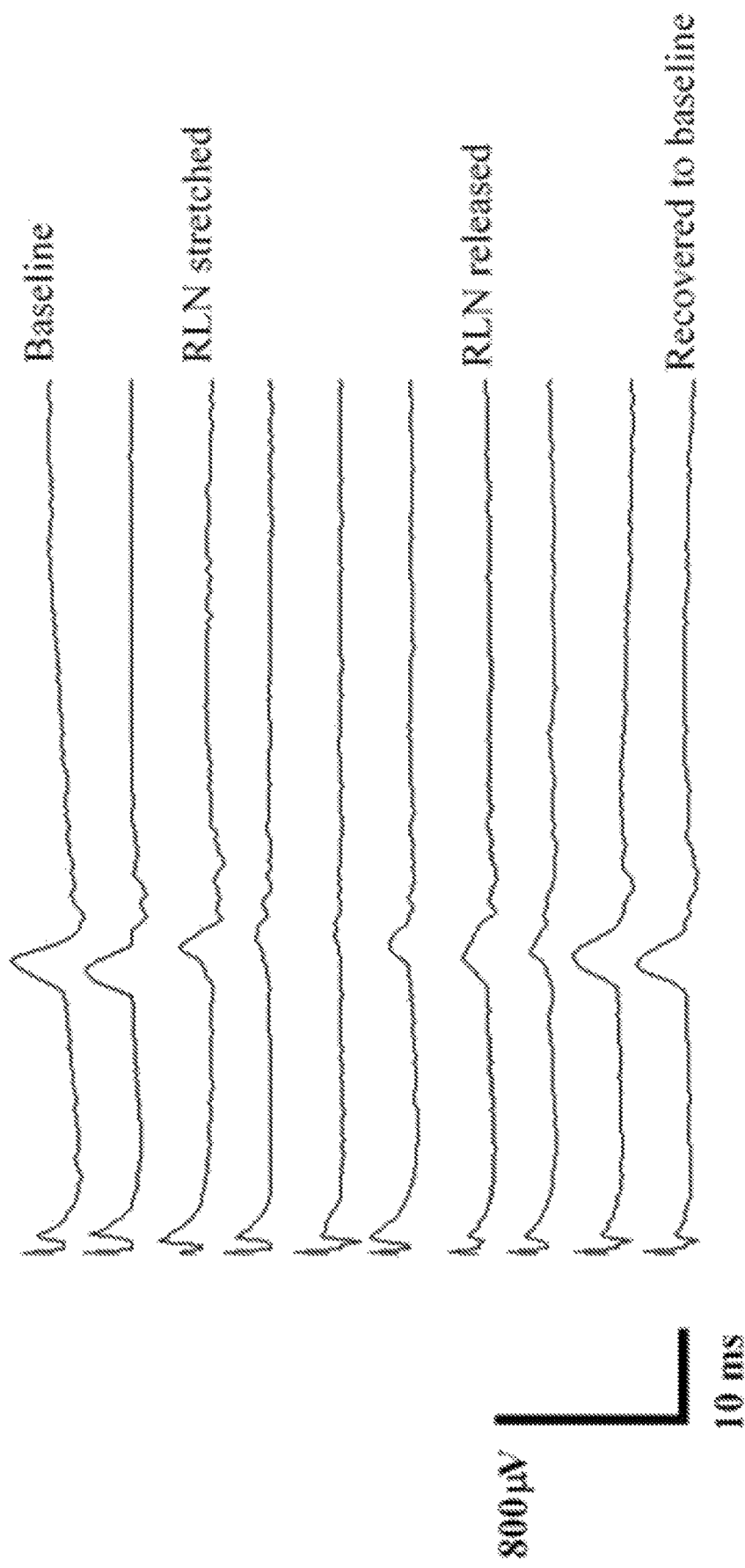
Figure 11:
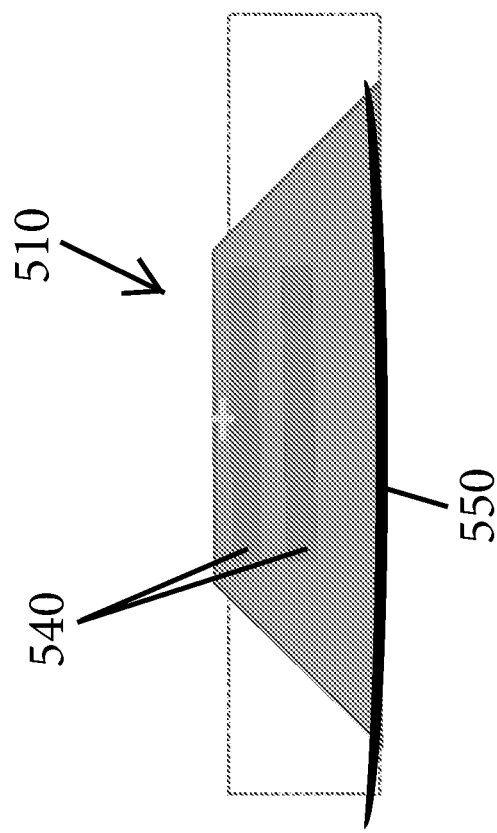
Figure 10:
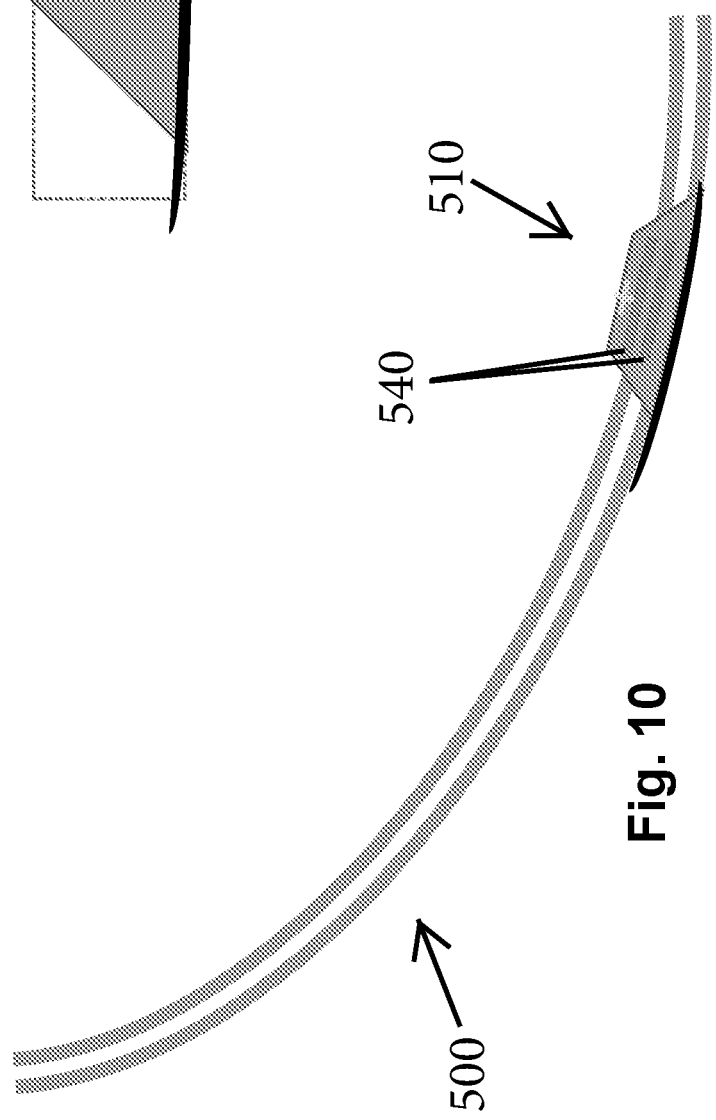
Figure 14:
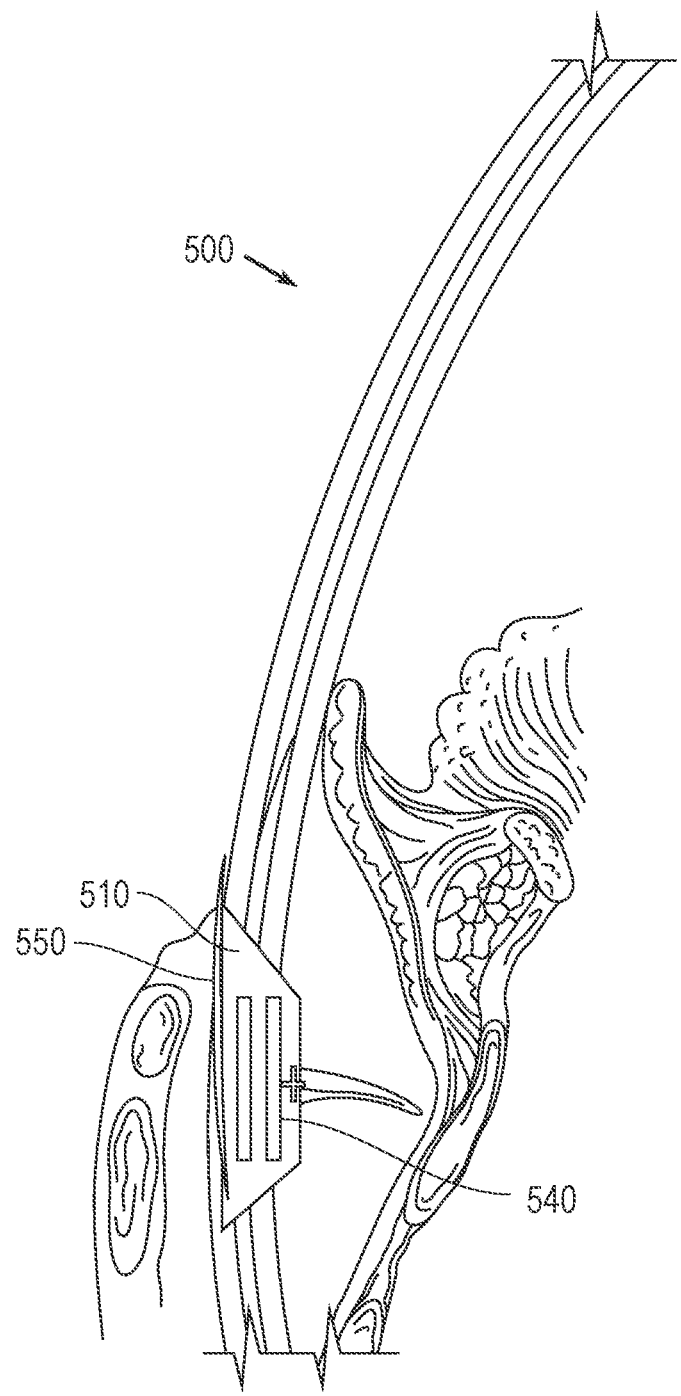
Figure 15:
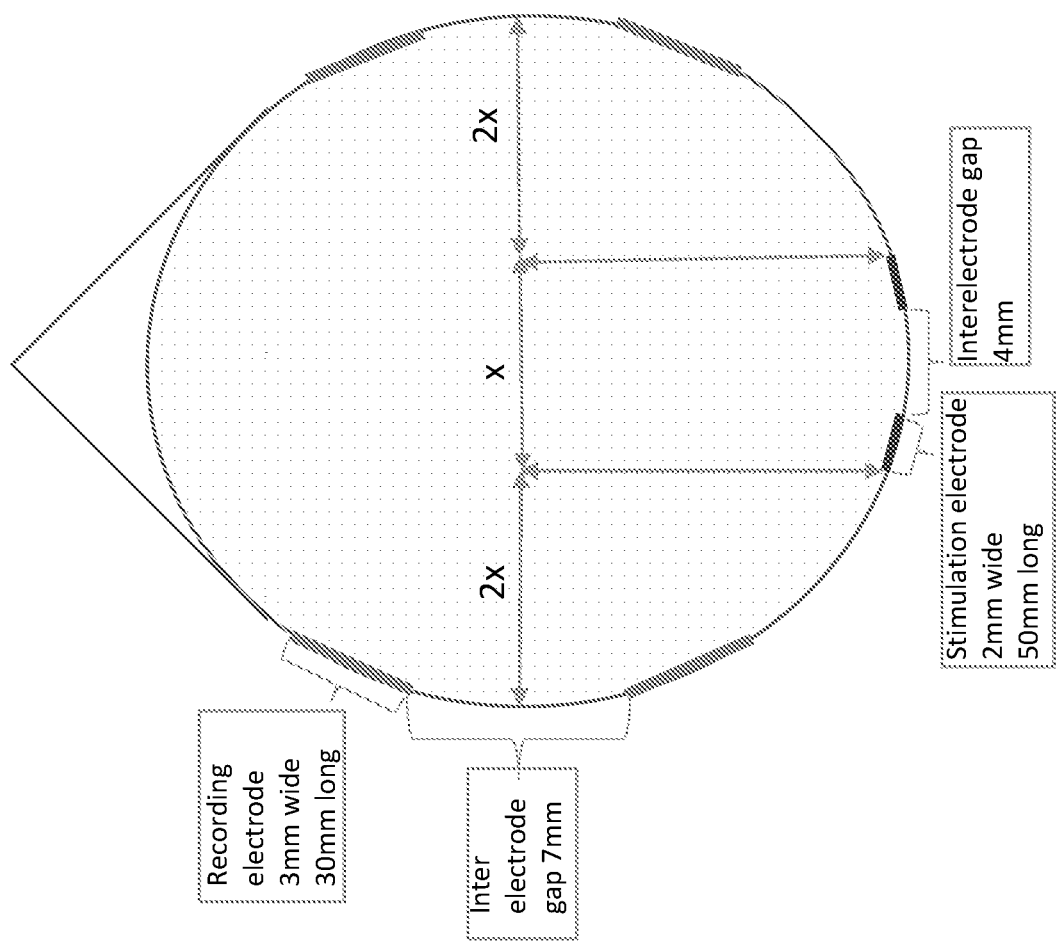
Figure 16:
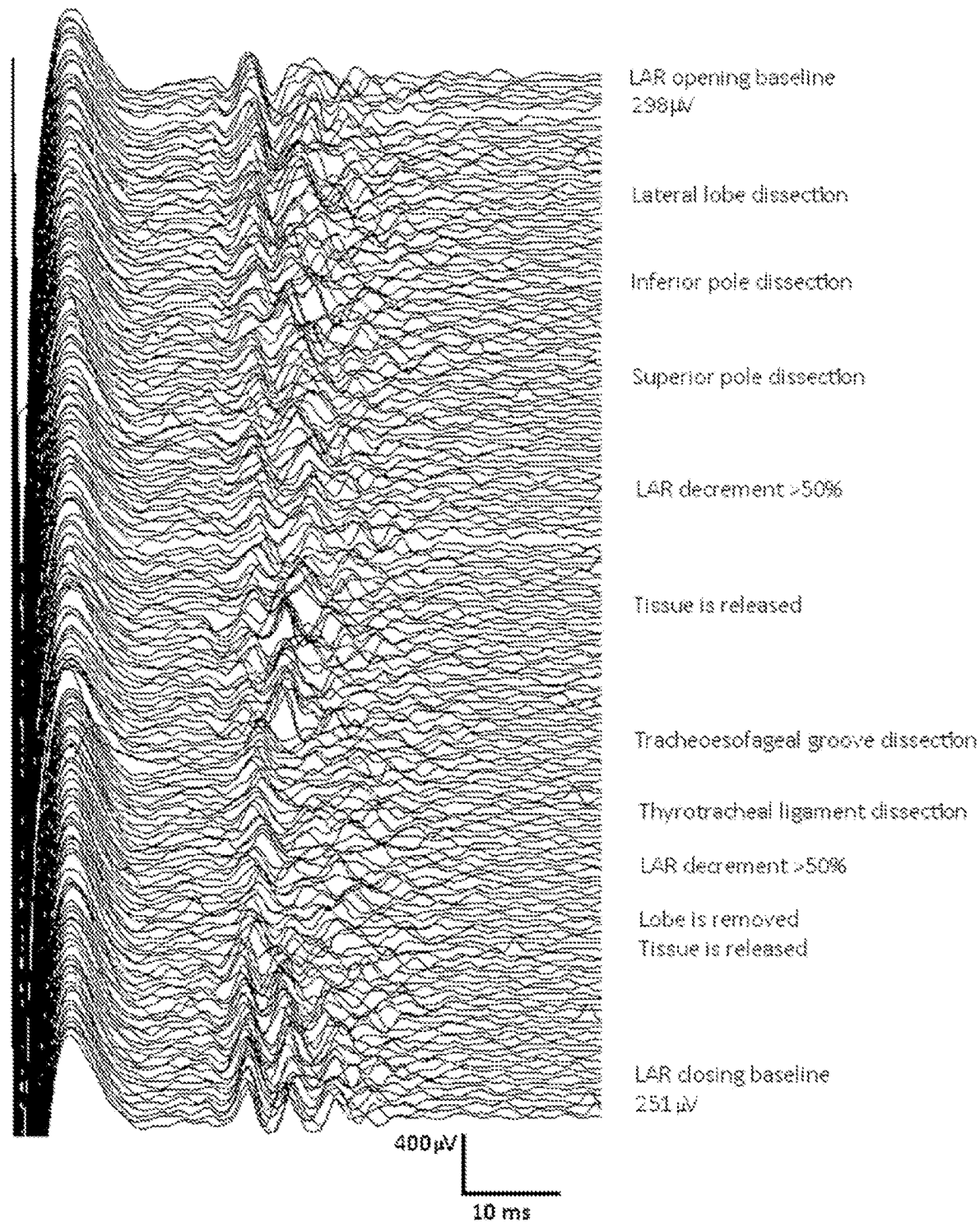

FIG. 7 is a schematic illustration showing results of one exemplary test group that shows traces of laryngeal adductor reflex in all fifteen patients under general anesthesia with TIVA. A single-stimulus or a pair stimuli (patients marked with *) at intensity up to 4 mA was applied. The cR1 response was reliably elicited throughout the surgery in all the patients. The cR2 response was elicited in 10 patients at the start of the surgery. Note the variability in the amplitude of the responses across the group probably due to the positioning of the endotracheal tube is of crucial importance;

FIG. 8 is a schematic illustration showing traces of the laryngeal adductor reflex in patient #8 from the test group of FIG. 7. Five consecutive trials, elicited at 0.7 Hz to avoid accommodation, are displayed in order to demonstrate the reproducibility of the reflex. The first five traces are superimposed at the bottom of the figure. In this case, contralateral R1 (black triangle) and R2 (white triangle) responses were persistently elicited illustrating that the LAR is a bilateral and robust reflex that can be successfully recorded in patients under general anesthesia with TIVA;

FIG. 9 is a schematic illustration showing 15 consecutive traces of the right laryngeal adductor reflex showing reversible changes of cR1 from baseline. The timing of these changes correlated temporally with surgical maneuvers that would have put stretch or compression directly on the RLN. The reflex recovered to baseline by simply relaxing the tissue;

FIG. 10 is a side elevation view of an intubation tube in accordance with another embodiment showing an electrode section thereof and for sake of simplicity a first cuff and optional second cuff are not shown;

FIG. 11 is an enlarged side elevation view that focuses of the electrode section of the intubation tube of FIG. 10;

FIG. 12 is a posterior perspective view of the electrode section of the intubation tube of FIG. 10;

FIG. 13 is a cross-sectional view of the electrode section of the intubation tube of FIG. 10;

FIG. 14 is partial cross-sectional view showing the intubation tube of FIG. 10 placed at a target treatment site;

FIG. 15 is a cross-sectional view of an exemplary electrode section of an intubation tube in accordance with the present invention; and FIG. 16 is an illustration of time course changes in LAR-CIONM traces during thyroid lobectomy.

DETAIL DESCRIPTION OF CERTAIN EMBODIMENTS

As used herein, the term "proximal" shall mean close to the operator (less into the body) and "distal" shall mean away from the operator (further into the body). In positioning a medical device inside a patient, "distal" refers to the direction away from an insertion location and "proximal" refers to the direction close to the insertion location.

Unless otherwise specified, all numbers expressing quantities, measurements, and other properties or parameters used in the specification and claims are to be understood as being modified in all instances by the term "about." Accordingly, unless otherwise indicated, it should be understood that the numerical parameters set forth in the following specification and attached claims are approximations. At the very least and not as an attempt to limit the application of the doctrine of equivalents to the scope of the attached claims, numerical parameters should be read in light of the number of reported significant digits and the application of ordinary rounding techniques.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In accordance with at least one exemplary embodiment, an intra-operative system and monitoring methodology for assessing the integrity of laryngeal and vagus nerves by utilizing the laryngeal adductor reflex (LAR) are provided.

As previously mentioned, the laryngeal adductor reflex (LAR) is an involuntary protective response triggered by sensory receptor stimulation in supraglottic (and glottic) mucosa. Afferent nerve activity travels via the internal branch of the superior laryngeal nerve (iSLN) to the brainstem. The efferent pathway is via the vagus and recurrent laryngeal nerves, resulting in vocal fold adduction and thus tracheobronchial airway protection. Vocal fold contractile components of the LAR consist of two parts—an early evoked R1 response with a latency between 16 and 18 ms, and later more variable R2 component. Prior studies had concluded that only ipsilateral R1 responses were present in humans under deep general anesthesia, with contralateral R1 and bilateral R2 responses being absent. However, as set forth below, the present Applicant recently showed using the device described herein that the contralateral R1 response is robustly present under total intravenous anesthesia, with the R2 response also present in a subset of patients. As also described herein, the LAR can alternatively be monitored by using the ipsilateral (iR1) component of the reflex for both stimulation and recording purposes. This monitoring is achieved using the endotracheal tubes with electrodes as described herein.

Detailed knowledge of the LAR has been difficult to obtain due to the perceived inability to successfully elicit all components of the reflex under general anesthesia. Studies in awake humans have been limited by laryngeal accessability issues, patient discomfort and inaccuracies in stimulation of the reflex. Whether threshold for elicitation of a bilateral LAR response differs between different laryngeal subsites remains unclear. In cats, it seems that most of the sensory receptors responsible for generating the reflex are located in the posterior laryngeal mucosa over the arytenoid cartilages (reference). However, we have very scarce data in humans and that which we do have is predominantly based on histological studies of sensory nerve receptor density. If there are topographical differences for LAR elicitation, this information could be used understand and potentially better manage conditions associated with impaired LAR functioning, including silent aspiration in the elderly and, possibly, sudden infant death syndrome. In addition, preventing complications of general anesthesia such as laryngospasm and aspiration are dependent on an understanding of which areas of the larynx are most responsible for eliciting the LAR. For example, if the posterior larynx in humans does indeed contain the highest density of sensory receptors, this is the area that should be targeted when topical local laryngeal anesthesia is applied to prevent laryngospasm. In accordance with one aspect of the present invention, the LAR is used to define the topography of the larynx as it relates to elicitation of the laryngeal adductor reflex using electrical mucosal stimulation under general anesthesia.

The general system and method described herein and according to at least one embodiment are used for a patient that is under general anesthesia of a type that does not suppress LAR. In other words, the present invention is implemented in general anesthesia regimes that preserve LAR and is not intended for use with general anesthesia that is of type that suppresses LAR. In one exemplary embodiment, the present system and method are used with patients that are under total intravenous anesthesia (TIVA).

As discussed herein, the LAR is a protective reflex that prevents aspiration by causing thyroarytenoid muscle contraction and thus vocal fold closure. It can be elicited via electrical stimulation of the iSLN or by stimulation of mechanoreceptors (or other receptors) in the laryngeal mucosa with air puffs. Recently, the LAR has been elicited by applying brief electrical stimulation directly to the laryngeal mucosa by a wire electrode passed through the laryngoscope until the mucosa is reached. In awake humans, the LAR consists of early (R1) and late (R2) bilateral responses and the R1 response has been shown to be present even during volitional vocal and respiratory tasks, attesting to the primordial and robust nature of this airway reflex.

Under general anesthesia, ipsi- and contralateral R1 responses (iR1 and cR1, respectively) have been observed in humans. However, the cR1 response tends to disappear at higher anesthetic levels of halogenated agents. The present invention provides a non-invasive, simple and reproducible methodology for eliciting the LAR under general anesthesia that relies solely on endotracheal tube-based surface electrodes. The present technique monitors not only vocal fold adduction but also the entire vagal reflex arc, incorporating for sensory, motor and brainstem pathways.

As discussed herein, LAR was successfully elicited under total intravenous anesthesia (TIVA) using surface based endotracheal tube electrodes that not only record but also stimulate. This is in contrast with previous methods in which endotracheal tube electrodes have been used only to record—but not stimulate. The present invention includes an endotracheal tube construction that improves IIONM and CIONM by improving signal specificity, increasing tissue contact with electrodes, and preventing rotation and proximal/distal movement of the endotracheal tube. The details of the improved endotracheal tube construction are discussed immediately below.

FIGS. 2-5 illustrate an intubation tube 100 in accordance with one exemplary embodiment of the present invention. As is known, tracheal intubation (intubation) is generally the placement of a flexible plastic tube into the trachea (windpipe) to maintain an open airway or to serve as a conduit through which to administer certain drugs. Intubation is frequently performed in the critically injured, ill, or anesthetized patients to facilitate ventilation of the lungs and to prevent the possibility of asphyxiation or airway obstruction. The most common technique (referred to as orotracheal) is to pass an endotracheal tube through the mouth, the vocal apparatus into the trachea. Because intubation is an invasive and uncomfortable medical procedure, intubation is usually performed after administration of general anesthesia and a neuromuscular-blocking drug. Intubation is normally facilitated by using a conventional laryngoscope, flexible fiber optic bronchoscope, or video laryngoscope to identify the vocal cords and pass the tube between the vocal cords into the trachea instead of into the esophagus. After the trachea has been intubated, a balloon cuff is typically inflated just above the distal end of the endotracheal tube to help secure it in place.

The illustrated intubation tube 100 is an elongated structure (tubular body 101) that includes a proximal end (not shown) that is located and positioned outside of the patient and a distal end 102 for insertion into the patient. The intubation tube 100 can be formed in any number of different sizes and can be formed to have any number of different shapes; however, a circular shape is most common. As described herein and illustrated in FIGS. 3A-C, the intubation tube 100 can have a variable cross-sectional shape in that one or more sections of the tube can have one shape (e.g., circular), while one or more other sections can have another, different shape (e.g., triangular).

One or More Inflatable Members

The intubation tube 100 includes a first inflatable member 110 and optionally includes a second inflatable member 120 that is spaced proximal to the first inflatable member 110. Due to their relative positions along the length of the intubation tube 100, the first inflatable member 110 can be referred to as being a lower balloon and the optional second inflatable member 120 can be referred to as being an upper balloon. The optional second inflatable member 120 is intended for placement at a location distal to the larynx and is configured for preventing proximal/distal movement of the intubation tube 100.

Each of the first and second inflatable members 110, 120 can be in the form of a balloon cuff that can be controllably and selectively inflated to a desired inflation level. It will be understood that the first inflatable member 110 can have a different shape and/or size compared to the second inflatable member 120.

Generally Triangular Shaped Electrode Section

As described herein, an area 200 between the first and second inflatable members 110, 120 of the intubation tube 100 can be in the form of an electrode section. More specifically, the area 200 is at least a recording electrode area that includes at least one first electrode 210 and at least one second electrode 220. The at least one electrode 210 is in the form of an active recording electrode and the at least one second electrode 220 is in the form of a reference recording electrode. The electrodes 210, 220 are described in more detail below. Alternatively and according to at least one other embodiment, the area 200 can include one or more stimulation electrode and thus, is not limited to only performing a recording function.

As described below, the area 200 preferably includes bi-lateral active electrodes that are configured to both provide stimulation and record tissue response depending upon the precise application (e.g., the location of the operative site) and therefore, there are at least two first electrodes 210, with at least one electrode 210 being on one side of the intubation tube 100 within the area 200 and the other electrode 220 is on the other side of the intubation tube 100 within the area 200.

Figure 2:
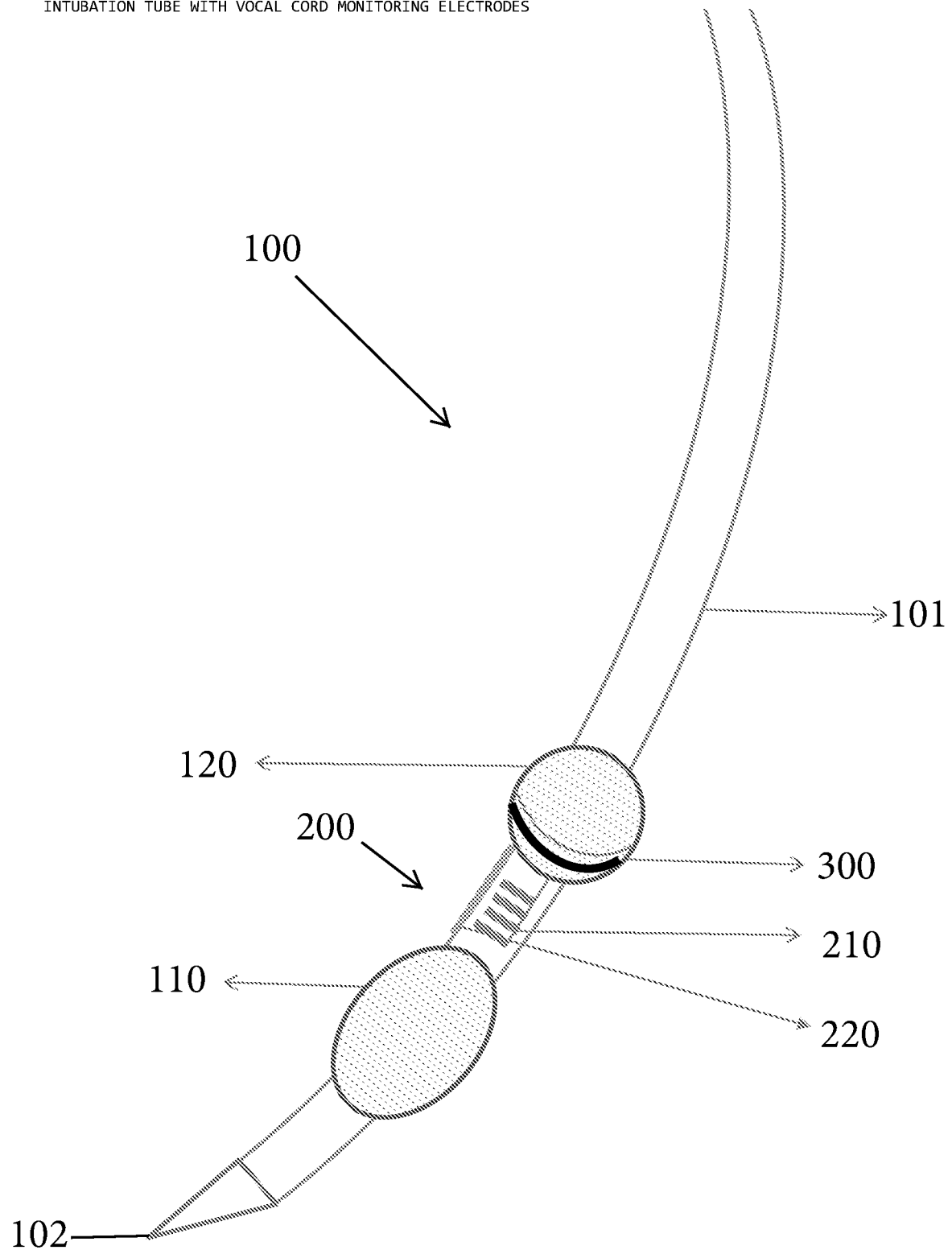
FIG. 2 is a side elevation view of an intubation tube with surface electrodes in accordance with one exemplary embodiment of the present invention.
Figure 3A:
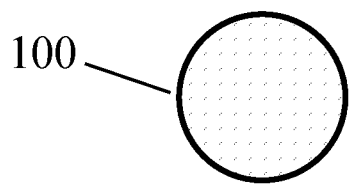
FIG. 3A is a first cross-sectional view taken through the intubation tube of FIG. 2.
Figure 3B:
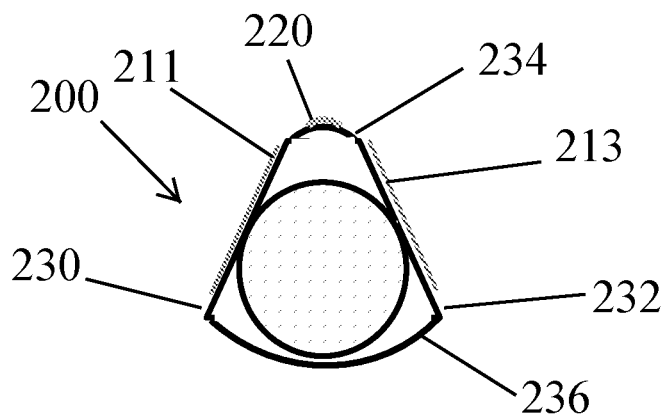
FIG. 3B is a second cross-sectional view taken through the intubation tube of FIG. 2.
Figure 3C:
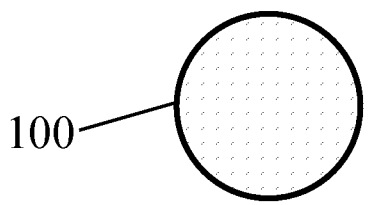
FIG. 3C is a third cross-sectional view taken through the intubation tube of FIG. 2.
Figure 3D:
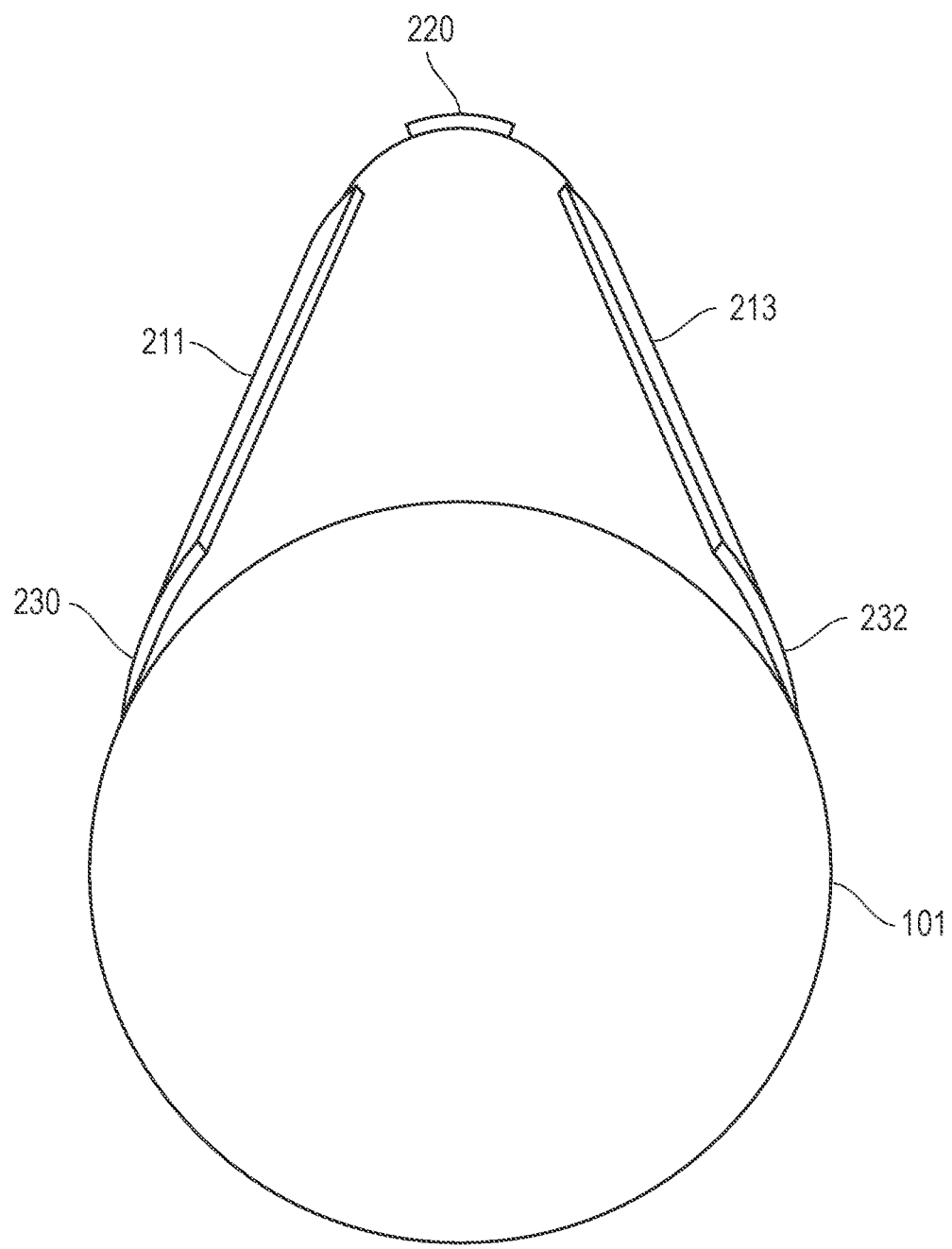
FIG. 3D is another cross-sectional view taken though an electrode area of the intubation tube according to yet another embodiment.

FIGS. 3A-3D illustrate exemplary constructions for the intubation tube 100. FIG. 3A shows that a cross-section of the intubation tube 100 at a location above the area 200 (and above the first inflatable member 110) is circular in shape. FIG. 3B shows that a cross-section of the intubation tube 100 at a location within the area 200 is generally triangular in shape. FIG. 3C shows that a cross-section of the intubation tube 100 at a location below the area 200 (and below the second inflatable member 120) is circular in shape. The generally triangular shape of the outer surface of the intubation tube 100 within the area 200 is configured to mate with the larynx anatomy and prevents rotation of the intubation tube 100, while also increasing the surface area of the intubation tube 100 that is contact with the larynx tissue. It will be understood that the generally triangular shape of the intubation tube 100 can be restricted to a front portion of the intubation tube as shown in FIG. 3D in that it is defined by an integral protrusion (extension) that has a triangular shape and extends radially outward from the circular shaped tube portion. The posterior aspect to the intubation tube is circular in shape similar to a conventional intubation tube as shown. The modification of the front portion (by inclusion of the triangular shaped protrusion in a discrete local region of the tube) allows for decreased left/right rotation, whilst not increasing the diameter of the posterior tube portion. As set forth below, this increased surface area allows for increased electrode-tissue contact.

FIGS. 2, 3B, 3D and 4 show details concerning the electrode section 200. As shown in FIG. 3B and described above, the intubation tube 100 has a generally triangular shaped cross-section in the area 200 (electrode section) that is defined by a first side surface (face) 230, an opposing second side surface (face) 232, a third side surface (face) 234, and an opposing fourth side surface (face) 236. A central, circular shaped bore is also formed in area 200. As shown, the first and second side surfaces 230, 232 can be planar surfaces that are angled with respect to one another, while the third and fourth side surfaces 234, 236 can be arcuate shaped. The third side surface 234 has an arcuate length that is less than the fourth side surface 236.

The reference recording electrode 220 can be a single electrode located along the third side surface 234 and more particularly, can be vertically oriented such that it extends longitudinally along a length of the intubation tube 100 within the area 200. The reference recording electrode 220 can be centrally oriented within the third side surface 234.

Figure 4:
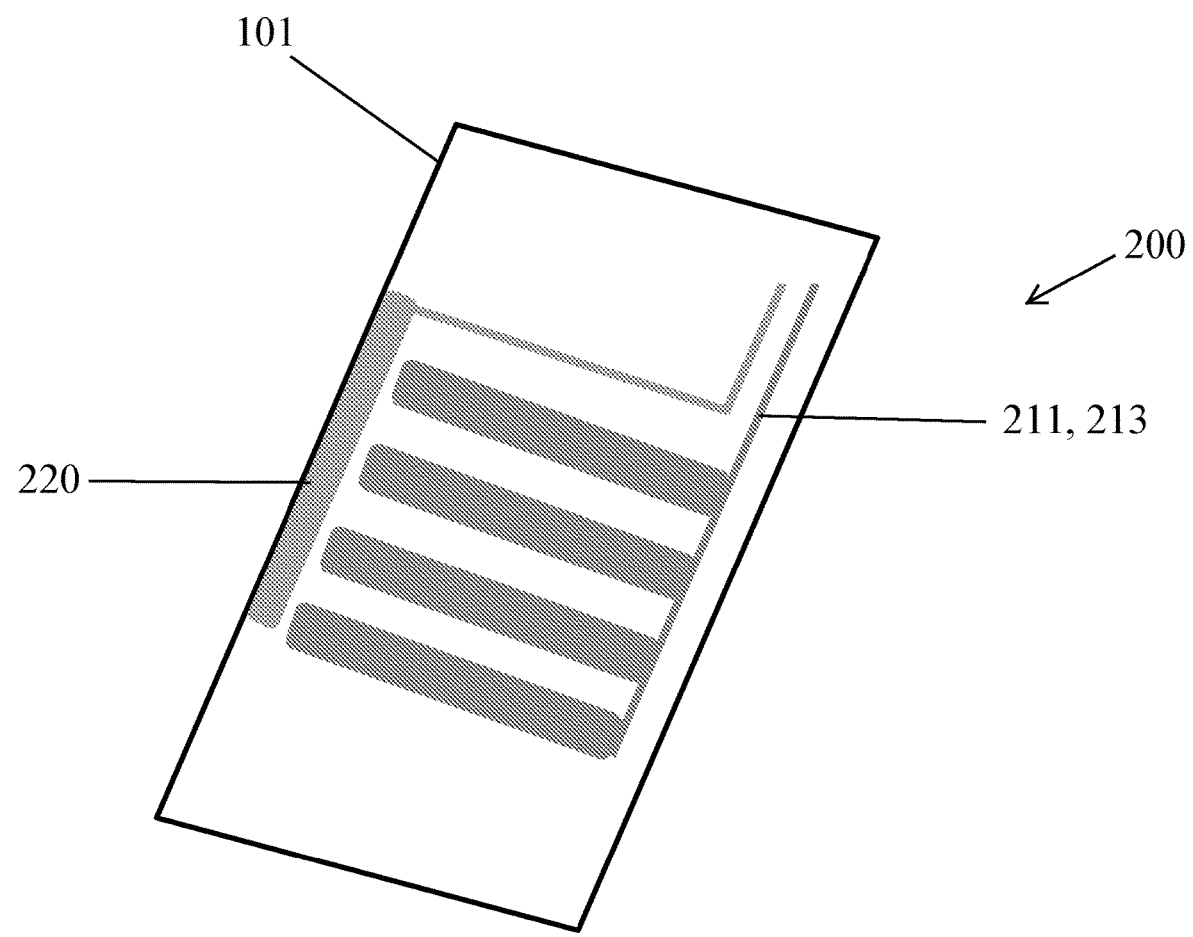
FIG. 4 is an enlarged view of a portion of the intubation tube of FIG. 2 showing a recording electrode section.
Figure 5:
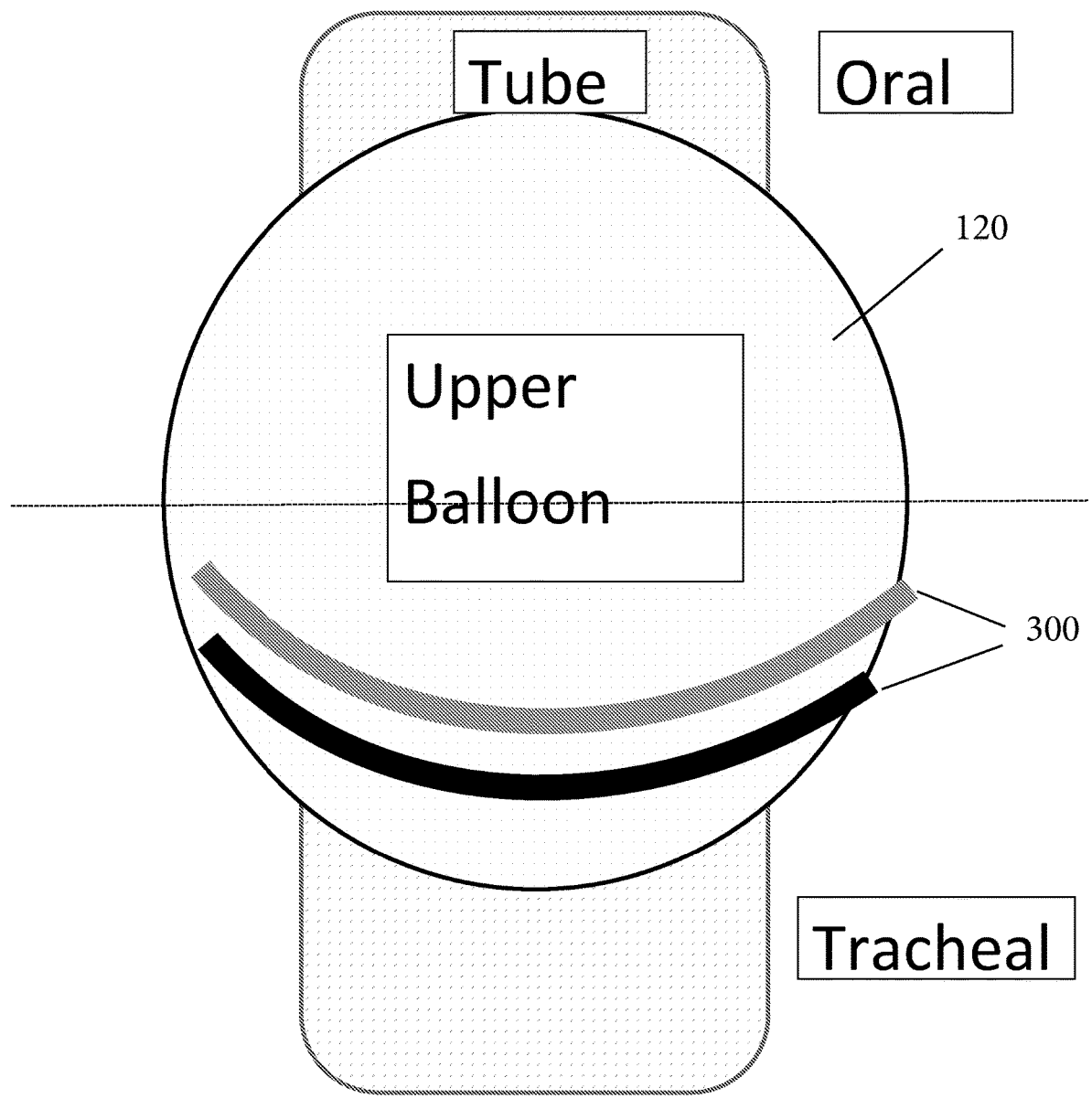
FIG. 5 is enlarged view of a portion of the intubation tube of FIG. 2 showing a stimulation electrode section.

In the illustrated embodiment, there is a plurality of active recording electrodes 210. The plurality of active recording electrodes 210 can be oriented parallel to one another and in series along a longitudinal length of the intubation tube 100 within the area 200 as shown. However, it will be understood that other arrangements of the active recording electrodes 210 are equally possible, including a vertical orientation or a matrix comprising rows and columns, and therefore, the electrodes 210 illustrated and described herein are merely exemplary in nature and not limiting of the scope of the present invention. More specifically and according to one embodiment, the active recording electrodes 210 are in the form of bi-lateral electrode arrays in that, as best shown in FIG. 3B, the active recording electrodes 210 can be formed of a first array 211 that is formed along the first side surface 230 and a second array 213 that is formed along the opposing second side surface 232. Each of the first and second arrays 211, 213 is defined by parallel spaced electrode bands disposed along the outer surface of the intubation tube 100 and electrically connected to one another, as shown in FIG. 4. As shown, each electrode band is operatively coupled to an electrical lead so as to electrically connect the electrode bands and permits a signal indicative of an LAR response to be delivered to a signal receiver (signal processor/recorder) that can record and/or analyze the signal as described below. In other words, electrode bands are electrically connected to the signal receiver.

In at least one embodiment, each of the first and second electrode arrays 211, 213 is configured to both provide an electrical stimulus (and thus acts as an active stimulation electrode) and also record signals, in this case, the contralateral R1 (cR1) and R2 (cR2) responses of the LAR (and thus act as an active recording electrode). The electrode arrays 211, 213 thus are configured to provide electrical stimuli to adjacent tissue by receiving electrical signal from a signal generator, which is described below, can be the same machine that records. As described herein and according to one exemplary implementation of the present system and method, the LAR was elicited by electrical stimulation of the laryngeal mucosa on the side contralateral to the operative field using the right or left surface electrodes (i.e., the first and second electrode arrays 211, 213) attached to the endotracheal tube 100 within area 200.

It will also be appreciated that as shown in FIG. 3D, the first and second electrode arrays 211, 213 can be disposed entirely along the faces 230, 232 that define the triangular shaped protrusion that extends radially outward from the circular shaped posterior portion of the intubation tube. The reference electrode 220 can also be positioned entirely within this triangular shaped portion as well.

When the second inflatable member 120 is used, the placement of the bi-lateral electrode arrays 211, 213 between the first and second inflatable members (cuffs) 110, 120 also improves the signal to noise ratio.

Stimulation Electrode

In one embodiment, the second inflatable member 120 includes one or more stimulation electrodes 300 that are disposed along an outer surface of the second inflatable member 120. See FIGS. 5 and 6. As shown, each stimulation electrode 300 extends about the outer surface (circumference) of the second inflatable member 120. The one or more stimulation electrodes 300 can be arranged in a latitudinal direction along the second inflatable member 120.

In one embodiment, there is a single stimulation electrode 300 disposed along the second inflatable member 120. When a single stimulation electrode 300 is used, it is configured such that it can provide electrical stimulation of the laryngeal mucosa on the side contralateral to the operative field and thus, has coverage over both the left vocal fold and the right vocal fold. As described herein, when the optional second inflatable member 120, with the at least one stimulation electrode 300, is used, the at least one stimulation electrode 300 then becomes the stimulating electrode of the system and the first and second electrode arrays 211, 213 become the recording electrodes. One advantage of this type of arrangement is that it allows left and right sides to be recorded simultaneously, something not possible with the only currently available continuous monitoring technique which requires a vagus nerve electrode to be placed on the ipsilateral side to operation field prior to being able to record continuously. In other words, by moving the active stimulation electrode from the area 200, the active electrodes in area 200, namely, the first and second electrode arrays 211, 213 serve only as recording electrodes, thereby providing bi-lateral recording coverage.

In one exemplary embodiment, the second inflatable member 120 has a bi-lateral electrode configuration in that there is one stimulation electrode 300 disposed along one side of the second inflatable member 120 and another stimulation electrode 300 is disposed along the other side of the second inflatable member 120. Each stimulation electrode 300 can be oriented in a latitudinal direction along the second inflatable member 120; however, other orientations are equally possible. The positions of the stimulation electrodes 300 are such that one stimulation electrode 300 is for placement into direct contact with the left vocal fold and the other stimulation electrode 300 is for placement into direct contact with the right vocal fold.

It will be understood that in yet another embodiment, the second inflatable member 120 is present along with the first inflatable member 110; however, the second inflatable member 120 is free of any stimulation electrodes and thus, serves only as an anchoring balloon to prevent proximal and distal movement of the intubation tube 100. In this embodiment, the stimulation electrode is thus one of the active electrodes 210 (e.g., first and second electrode arrays 211, 213) that is located within area 200 of the intubation tube 100 and the recording electrode is the other of the active electrodes 210.

Stimulus Generator/Recording Device (Machine or System)

Figure 6:
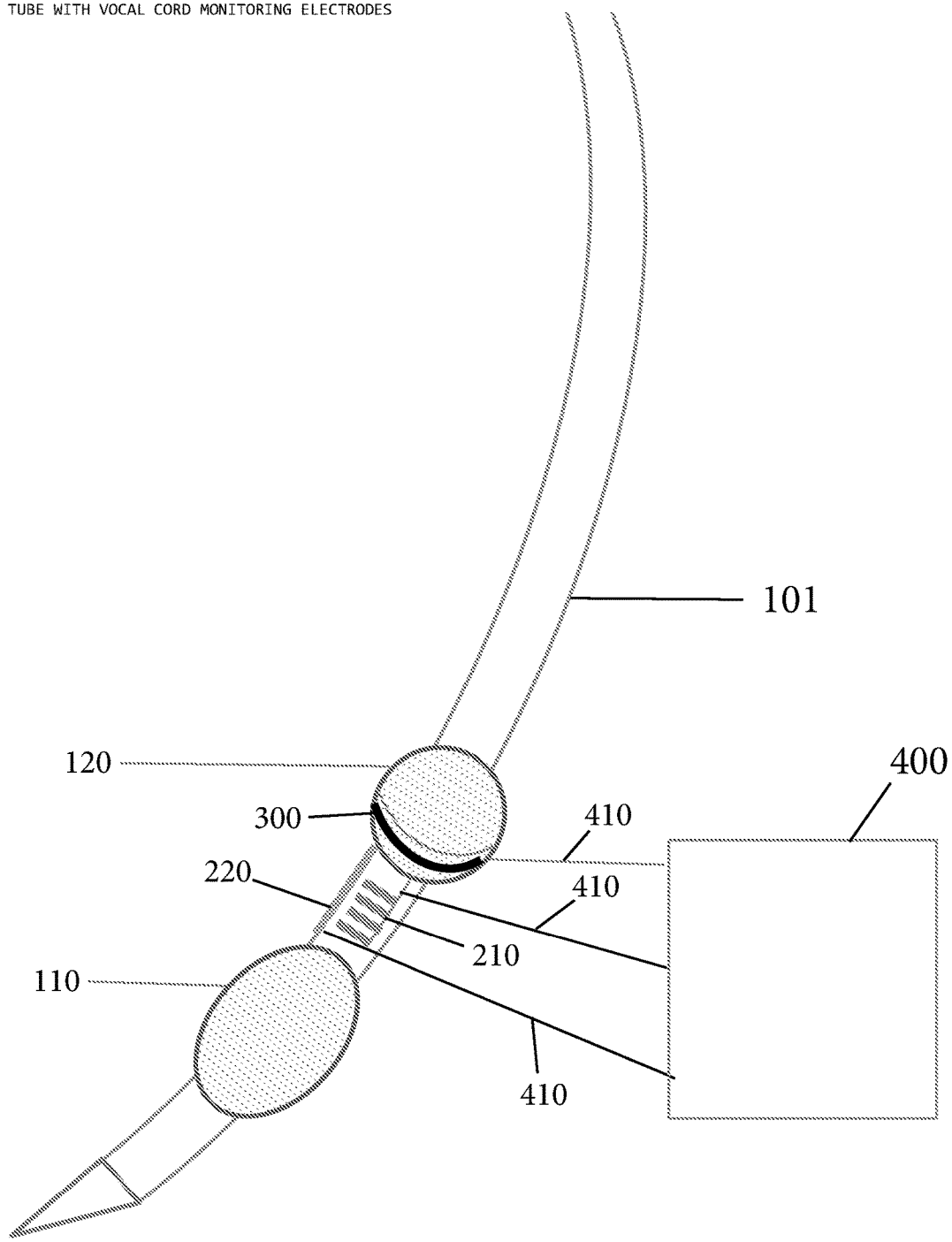
FIG. 6 shows the intubation tube of FIG. 2 electrically connected to a machine that is configured to generate electrical stimuli and record responses (electrical signals)

As best shown in FIG. 6, each of the electrodes associated with the intubation tube 100 is electrically connected to a machine 400 that is configured to both generate stimuli and record responses to the applied stimuli (e.g., electric signals). The electrical connection between the individual electrodes and the machine 400 is by conventional means, such as wires or other type of connectors 410. The machine 400 can thus be a signal generator/receiver that is suitable for the present application in that it is configured to both generate electrical stimuli (electrical signals) and record electrical signals.

One exemplary machine 400 is an Axon Sentinel 4 EP Analyzer machine (Axon Systems Inc.; Hauppauge, N.Y., USA) that comprises a multi-channel device that monitors and detects electrical signals (e.g., evoked potential monitoring) and is further configured to emit electrical signals (stimulation signals). Signals received by the machine 400 can be amplified, filtered and then stored on a computer device, such as a desk-top or laptop, or can be stored in the cloud (network). As described below, the machine 400 is configured such that the electrical stimuli can be directed to one or more electrodes and the character of the electrical stimuli can be controlled by the user, e.g., the frequency, duration, etc., of the electrical stimuli can be selected and controlled.

EXAMPLE 1

Patient Study

Fifteen patients who underwent neck surgery were studied. Table 1 (set forth below) shows demographics, diagnosis and type of surgery for each patient. The anesthetic regimen consisted of total intravenous anesthesia (TIVA) using propofol and remifentanil in standard weight based doses.

After induction of general anesthesia, the patient was intubated with a Nerve Integrity Monitor TriVantage endotracheal tube (NIM TriVantage™, Medtronics Xomed Inc.; Jacksonville, Fla., USA) containing bilaterally imbedded conductive silver ink surface electrodes (See, FIGS. 1A-1C). These electrodes come into direct contact with the right and left vocal folds (FIGS. 1A and 1B). It will be appreciated that both the intubation tube construction and the electrode construction and placement in FIGS. 1A and 1B is different than the embodiment shown in FIGS. 2-6. More specifically, FIGS. 1A and 1B depict an intubation tube 10 having a first inflatable member (balloon cuff) 20, a first pair of electrodes 30 on one side (e.g., left) of the tube 10, and a second pair of electrodes 40 on the other side (e.g., right) of the tube 10.

Following initial intubation, the tube position was rechecked after the patient was properly positioned for the neck surgery. For stimulation and recording, an Axon Sentinel 4 EP Analyzer machine was utilized (Axon Systems Inc.; Hauppauge, N.Y., USA). This type of device is a multi-channel device that monitors and detects electrical signals (evoked potential monitoring). Other suitable machines can equally be used. The LAR was elicited by electrical stimulation of the laryngeal mucosa on the side contralateral to the operative field using the right or left surface electrodes attached to the endotracheal tube.

It will therefore be appreciated that unlike in conventional uses, the intubation tube 10 shown in FIGS. 1A and 1B was operatively connected to a machine (e.g., the Axon Sentinel 4 EP Analyzer machine) that is configured not only to record but also to generate and deliver stimuli to certain select electrodes. For example, the electrode(s) on one side of the tube can be selected as being a stimulating electrode(s) and the device to which the electrode(s) is electrically connected thus supplies electrical stimuli to this electrode. The electrode(s) on the other side of the tube would thus be selected and serve as the recording electrode(s). This is in direct contrast to the conventional use of the illustrated intubation tube in which both the left and right electrodes act only as recording electrodes.

A single stimulus (0.1-1 ms duration) or a pair of stimuli (ISI 2-4 ms) at intensity up to 4 mA was applied. In order to minimize stimulus artifact, two responses elicited by stimuli of reverse polarity were averaged. Surface electrodes ipsilateral to the surgical field (and contralateral to the stimulation side) attached to the endotracheal tube were used to record the contralateral R1 (cR1) and R2 (cR2) responses of the LAR. The cR1 and cR2 responses were defined as the short and long-latency responses, respectively, elicited in the contralateral vocal fold muscles relative to the stimulating side (FIG. 1C). Signals were amplified (4000), filtered (bandwidth 1.5-1000 Hz), and stored on the computer for off-line analysis.

The results of the study described above are as follows. There were three males and twelve females aged between 28 and 84 years (55±20, mean±SD). In all patients, LARs were successfully elicited bilaterally. The cR1 response was reliably elicited throughout the surgery in all cases (FIGS. 1A-1C). A cR2 response was also seen in 10 patients. The mean onset latency and amplitude (measured peak to peak) of the cR1 response for the right and left vocal folds are presented in Table 2 (set forth below). The mean onset latency of the elicited cR2 response is also presented.

The intensity of current required to elicit the LAR varied between 2 mA (0.1 ms duration) to 4 mA (1 ms duration) and the intensity required to elicit the reflex for each patient was adjusted throughout the surgery to obtain reliable cR1 responses. Reversible changes in the LAR manifesting as increased latency and decreased amplitude of response from baseline were noted to occur during every surgery. In every surgery, the timing of these changes correlated temporally with surgical maneuvers that would have put stretch or compression directly on the RLN. During times when the RLN was out of the operative field, the LAR remained constant in amplitude and latency. None of the patients had intraoperative total reflex loss and, postoperatively, no patient had objective vocal cord paralysis. No intra-operative or post-operative complications relating to the stimulation or recording of the LAR were noted for any patient.

The above-described study demonstrates the feasibility of monitoring both sensory and motor pathways of the laryngeal nerves during neck surgery by eliciting the LAR in patients under total intravenous general anesthesia. This novel methodology is simple, noninvasive and widely applicable as it uses a commercially available endotracheal tube for stimulating laryngeal mucosa on one side and recording contralateral vocal fold responses on the opposite side (cR1 and cR2).

Using this methodology, the present Applicant was successfully able to assess the functional integrity of the LAR pathways throughout all included neck surgeries. This laryngeal reflex thus represents a new method for continuous monitoring of vagal and recurrent laryngeal nerve function. The LAR is a brainstem reflex that protects the larynx from aspiration. Afferent and efferent limbs of the LAR are mediated by two distinctive branches of the vagus nerve, the SLN and the RLN. The afferent limb carries information from sensory receptors in the supraglottic and glottic mucosa (likely mechanoreceptors and chemoreceptors) through the iSLN. The inferior glottis and subglottic regions of the larynx receive sensory fibers from the RLN which may also contribute to the reflex during mucosal stimulation with surface based endotracheal tube electrodes. The efferent limb of the LAR is mediated by motor fibers of the RLN.

Prior studies have shown that electrical stimulation of the iSLN induces several recordable responses in adductor muscles of the larynx. An early ipsilateral response (relative to the stimulus) called ipsilateral R1 (iR1) has been extensively recorded in anesthetized cats, dogs, pigs and humans. A short latency contralateral R1 response (cR1) that involves contralateral adduction of the vocal fold muscle has been consistently recorded in anesthetized cats, awake humans, and humans under low dose of general anesthesia. A longer latency R2 response that produces bilateral vocal cord adduction have been recorded in awake humans. Latency of iR1 in awake and anesthetized humans is typically between 13-18 ms (milliseconds). It has also been noted that the latency of the human cR1 response is approximately 4 ms longer than the latency of the iR1 response, and proposed different models of brainstem circuitry for iR1 and cR1 responses. The iR1 was proposed to project from the iSLN to motor neurons of the ipsilateral nucleus ambiguus via the ipsilateral nucleus of the tractus solitarius. In contrast, the cR1 would project from the ipsilateral nucleus of the tractus solitarius to the contralateral nucleus ambiguous via 2-3 additional interneuron synapses within the reticular formation, thus giving the contralateral adduction of the reflex. The presence of the cR1 response would be supported by central facilitation and consequently would be suppressed by anesthesia in a dose-dependent manner Subsequently, due to this perceived difficulty in eliciting contralateral responses in animals (except for the cat) and humans under deep general anesthesia, other studies do not address cR1 responses despite the LAR being a bilateral reflex. In the present study, Applicant provides evidence of the feasibility of eliciting cR1 responses in patients under general anesthesia with TIVA, similar to the cR1 responses that Sasaki et al (2003) were able to elicit at 0.5 MAC of isoflurane 10 (but not at higher alveolar concentrations). The ability to elicit the cR1 in 100% of patients under TIVA attests to robust nature of this reflex as an airway protective mechanism.

Currently available methods for continuous intraoperative monitoring of the RLN rely on operative exposure of the RLN and/or vagus nerves for placement of monitoring probes. The ability to use the surface electrodes of the endotracheal tube for stimulation and recording purposes without requiring placement of additional monitoring devices within the neck is thus a tremendous advantage over other currently available techniques. The ability to obtain continuous nerve integrity feedback without actual nerve exposure also broadens the potential uses of this technique to surgical procedures where the RLN (or iSLN) is at risk but not necessarily directly visualized in the operative field. In addition, this methodology has the ability to assess intraoperative afferent laryngeal nerve function, something that is lacking in previous methodologies. Brainstem and basis crania surgeries frequently pose a significant risk to the integrity of the vagus nerve. Current methodologies for intra-operative monitoring include cranial nerve mapping of the vagus nerve and cortico-bulbar motor evoked potentials (MEP). Cranial nerve mapping is one of the most utilized methodologies but depends on surgeon participation and cannot be used continuously. Cortico-bulbar MEPs can continuously assess the integrity of nerves, nuclei and central pathways if used frequently however they provoke movement due to transcranial electrical stimulation that interrupts the surgery and thus the frequency of application is limited. In contrast, the LAR is simple to perform and does not evoke movement or cause any disruption to the surgical procedure. However, it must be noted that although it assesses integrity of the vagus nerve and nucleus ambiguous it cannot assess the integrity of supranuclear pathways. Positioning of the electrodes on the endotracheal tube is of crucial importance to the success of this reflex. The electrodes must be positioned so that they oppose the glottic mucosa for both stimulation and recording purposes. There have been prior articles describing how the tube should be positioned during thyroid surgery and these guidelines are helpful in ensuring correct tube placement. If intraoperative changes in the reflex occur (decrease in amplitude or increase in latency compared to baseline recordings) during surgery where laryngeal nerves are at risk, several factors need to be addressed. First, stimulus intensity should be increased until reflex trace returns to baseline levels because threshold for eliciting the LAR may have changed due to surgical manipulations. If increasing intensity does not recover the reflex to baseline recordings, the surgeon should be alerted and asked if the nerve is being stretched at that moment. If so, simply relaxing the tissue may allow the reflex to recover. If releasing the tissue does not result in full recovery or if the surgeon is not operating near the nerve at the time, tube position should be checked. The tube position is optimally checked by using a laryngoscope however it can also be checked without using laryngoscopy by moving the tube in a rotational or proximal-distal direction and testing the reflex in each new tube position. Finally, if none of the above maneuvers recovers the reflex to baseline levels, true reflex changes due to impending nerve injury can be suspected. Loss of the LAR is a warning criteria for the surgeon to stop the surgery and explore the surgical field to confirm nerve injury.

TABLE 1

| Patient | Gender | Age | Diagnosis | Surgery |
| --- | --- | --- | --- | --- |
| 1 | F | 35 | Left thyroid goiter | Left thyroidectomy |
| 2 | M | 50 | Thyroid carcinoma metastatic | Total thyroidectomy |
| 3 | F | 78 | Spondylolisthesis | Anterior cervical discectomy and fusion |
| 4 | F | 80 | Hypoparathyroidism | Parathyroidectomy |
| 5 | F | 28 | Thyroid inflammatory disease with thyroid goiter | Total thyroidectomy |
| 6 | F | 63 | Thyroid nodules | Total thyroidectomy |
| 7 | F | 79 | Right thyroid carcinoma | Total thyroidectomy |
| 8 | F | 70 | Right thyroid goiter | Right thyroidectomy |
| 9 | F | 31 | Thyroid goiter | Total thyroidectomy |
| 10 | F | 49 | Thyroid goiter | Total thyroidectomy |
| 11 | M | 55 | Left thyroid nodule | Left thyroidectomy |
| 12 | F | 35 | Right thyroid nodule | Right thyroidectomy |
| 13 | M | 35 | Thyroglossal duct cyst | Excision of left thyroglossal duct cyst |
| 14 | F | 57 | Right thyroid nodule | Right thyroidectomy |
| 15 | F | 84 | Hypoparathyroidism | Parathyroidectomy |

M: male; F: female; Age expressed in years.

TABLE 2

| | Contralateral R1 | | | | Contralateral R2 | |
| --- | --- | --- | --- | --- | --- | --- |
| | Right VF recording | | Left VF recording | | Right VF recording | Left VF recording |
| | Latency (ms) | Amplitude (uV) | Latency (ms) | Amplitude (uV) | Latency (ms) | Latency (ms) |
| Mean | 22.4 | 243.4 | 22.2 | 222.7 | 61.1 | 59.9 |
| SD | 2.5 | 122.6 | 2.4 | 136.3 | 7.0 | 6.1 |
| Maximal | 25.9 | 528.6 | 27.1 | 495.4 | 70.6 | 71.8 |
| Minimum | 17.6 | 95.2 | 18.4 | 81.0 | 53.3 | 53.3 |

VF: vocal fold

Based on at least the foregoing study, intra-operative application of the LAR using endotracheal tube surface based electrodes and contralateral R1 responses is a viable method of monitoring recurrent laryngeal and vagus nerve integrity during surgery. The results from the above study indicate that the LAR was reliably elicited in 100% of patients for the duration of each surgical procedure. Mean onset latency of cR1 response was 22.4+/−2.5 ms (right) and 22.2+/−2.4 ms (left). cR2 responses were noted in 10 patients (66.7%). No peri-operative complications or adverse outcomes were observed.

As a result, the LAR is a novel neuro-monitoring technique for the vagus nerve and in particular, represents a novel method for intraoperatively monitoring laryngeal and vagus nerves. The LAR monitors the entire vagus nerve reflex arc and is thus applicable to all surgeries where vagal nerve integrity may be compromised. Advantages over current monitoring techniques including simplicity, ability to continuously monitor neural function without placement of additional neural probes and ability to assess integrity of both sensory and motor pathways.

FIGS. 10-14 illustrate an alternative intubation tube 500 according to another embodiment. The intubation tube 500 is similar to intubation tube 100 and is in the form of an elongated structure (tubular body) that includes a proximal end (not shown) that is located and positioned outside of the patient and a distal end for insertion into the patient. The intubation tube 500 can be formed in any number of different sizes and can be formed to have any number of different shapes; however, a circular shape is most common. Like the intubation tube 100, the intubation tube 500 can have a variable cross-sectional shape in that one or more sections of the tube can have one shape (e.g., circular), while one or more other sections can have another, different shape (e.g., triangular as described below).

One or More Inflatable Members

Also like the intubation tube 100, the intubation tube 500 includes a first inflatable member 110 (see, FIG. 2) and optionally includes a second inflatable member 120 (see, FIG. 2) that is spaced proximal to the first inflatable member 110. For sake of simplicity, the first and second inflatable members 110 120 are not shown in FIG. 10. It will be appreciated that an electrode section (electrode area) 510 shown in FIGS. 10-12 is positioned between the first and second inflatable members along the elongated body of the intubation tube 500.

Generally Triangular Shaped Electrode Section

As described herein, the electrode section or area 510, which can be located between the first inflatable and second inflatable members 110, 120 (FIG. 2) of the intubation tube 500 can be in the form of an electrode section. More specifically, the electrode area 510 is configured as a multi-functional electrode section. In particular, unlike the previous embodiment in which the stimulation electrodes were placed on the second cuff (second inflatable member 120), the electrode area 510 includes both recording and stimulation electrodes as described in detail below.

As shown, the electrode area 510 is generally triangularly shaped like electrode section 200 of the previous embodiment. As shown in FIGS. 12 and 13, within the electrode area 510 of the intubation tube 500, the intubation tube has a first portion 520 that is generally circular in shape and an adjacent second portion 530 that protrudes radially outward from the first portion 520.

FIGS. 10-12 illustrate exemplary constructions for the intubation tube 100. It will be appreciated like the previous embodiment, a cross-section of the intubation tube 500 at a location above the area 510 (and above the first inflatable member 110 (FIG. 1)) is circular in shape. FIG. 13 shows that a cross-section of the intubation tube 500 at a location within the area 510 is generally triangular in shape. It will further be appreciated that like the previous embodiment, a cross-section of the intubation tube 500 at a location below the area 510 (and below the second inflatable member 120 (FIG. 1)) is circular in shape. The generally triangular shape of the outer surface of the intubation tube 500 within the area 510 is configured to mate with the larynx anatomy and prevents rotation of the intubation tube 500, while also increasing the surface area of the intubation tube 500 that is contact with the larynx tissue. It will be understood that the generally triangular shape of the intubation tube 500 can be restricted to a front portion of the intubation tube as shown in FIGS. 12 and 13 in that it is defined by an integral protrusion (extension) that has a triangular shape and extends radially outward from the circular shaped tube portion. The posterior aspect to the intubation tube is circular in shape similar to a conventional intubation tube as shown. The modification of the front portion (by inclusion of the triangular shaped protrusion in a discrete local region of the tube) allows for decreased left/right rotation, whilst not increasing the diameter of the posterior tube portion. As set forth below, this increased surface area allows for increased electrode-tissue contact.

FIGS. 10-14 show details concerning the electrode section 510. As shown in FIG. 13 and described above, the intubation tube 500 has a generally triangular shaped cross-section in the area 510 (electrode section) that can generally be thought of as including a first side surface (face) 522, an opposing second side surface (face) 524, a third side surface (face) 526 which is an anterior portion, and an opposing fourth side surface (face) 528 which is a posterior portion. A central, circular shaped bore is also formed in area 510. As shown, the first and second side surfaces 522, 524 can be slightly curved or planar surfaces that are angled with respect to one another, while the third and fourth side surfaces 526, 528 can be arcuate shaped. The third side surface 526 has an arcuate length that is less than the fourth side surface 528.

Recording Electrodes

The electrode area 510 includes a plurality of recording electrodes and in particular, includes at least one first electrode 530 in the form of an active recording electrode and the at least one second electrode 540 in the form of a reference recording electrode. The electrodes 530, 540 are described in more detail below.

The electrode area 510 preferably includes bi-lateral active electrodes that are configured to both provide stimulation and record tissue response depending upon the precise application (e.g., the location of the operative site) and therefore, there are at least two recording electrodes, with at least one electrode being on one side of the intubation tube 500 within the area 510 and at least one electrode being on the other side of the intubation tube 500 within the area 510.

In the illustrated embodiment, one recording electrode 530 is located on the first side 522, while one recording electrode 540 is located on the opposite side 524. As shown, there are preferably a pair of recording electrode 530 on the first side 522 and a pair of electrodes 540 on the second side 524. The electrodes 530 can run longitudinally along the intubation tube 500 and are parallel to one another and similarly, the electrodes 540 can run longitudinally along the intubation tube 500 and are parallel to one another. As best shown in FIGS. 12 and 13, one electrode 530 is proximate the anterior (generally triangular shaped) protrusion, while the other electrode 530 is located along the circular shaped body closer to the posterior side. The same is true for the pair of electrodes 540 in that one can be located proximate the anterior protrusion with the other being closer to the posterior side.

FIG. 11 shows a side (lateral) view of the electrode area 510 and it can be seen that from the side view, one pair of recording electrodes (in this case electrodes 540) can be seen (from the other side view, the other pair of electrodes 530 can be seen).

Stimulation Electrodes

In the illustrated embodiment and in contrast to the previous embodiments, the electrode area 510 includes one or more stimulation electrodes 550 that are disposed along an outer surface of the intubation tube 500 within the electrode area 510 as shown in the figures. The illustrated embodiment includes a pair of stimulation electrodes 550 that are located along the fourth side 528 (posterior side) of the intubation tube 500. Like the recording electrodes 530, 540, the stimulation electrodes 550 can run longitudinally and are spaced apart (in a parallel manner).

While the lengths of the recording electrodes 530, 540 and the stimulation electrodes 550 are shown as generally be equal and the widths are shown as generally being equal, it will be appreciated that the lengths and/or widths can be different.

As a result of the posterior positioning and use of a pair of stimulating electrodes 550, the stimulating electrodes 550 become the stimulating electrodes of the system and the first and second electrode arrays 230, 240 become the recording electrodes. One advantage of this type of arrangement is that it allows left and right sides to be recorded simultaneously, something not possible with the only currently available continuous monitoring technique which requires a vagus nerve electrode to be placed on the ipsilateral side to operation field prior to being able to record continuously. The first and second electrode arrays 530, 540 serve only as recording electrodes, thereby providing bi-lateral recording coverage.

In illustrated embodiment, the electrode area 510 also has a bi-lateral electrode configuration in that there is one stimulation electrode 550 disposed along one side of the electrode area 510 and another stimulation electrode 550 is disposed along the other side of the electrode area 510.

The design of the intubation tube 500 improves IIONM and CIONM by improving signal specificity, increasing tissue contact with electrodes, and preventing rotation and proximal/distal movement of the intubation tube 500.

The optional second inflatable member (balloon or cuff) 120 (FIG. 2) can be positioned along the intubation tube 500 at a location that will be distal to the larynx for preventing proximal/distal movement.

As mentioned previously, the triangular outer surface of the intubation tube 500 between cuffs (first and second inflatable members of FIG. 1) mates with the larynx anatomy and therefore, prevents rotation and increases electrode-tissue contact.

The placement of bi-lateral electrode arrays (e.g., the bi-lateral recording electrodes 530, 540 and bi-lateral stimulation electrodes 550) between the cuffs (first and second inflatable members of FIG. 1) improves signal to noise ratio.

As shown in FIG. 14, the stimulation electrodes 550 can, in the illustrated embodiment, be thought of as being posterior arytenoid rim stimulation electrodes. The illustrated intubation tube 500 allows for bilateral reflex recording. The illustrated intubation tube 500 thus includes a total of 6 electrodes (3 pairs) with 4 electrodes (2 pairs) being recording electrodes and 2 electrodes (1 pair) being stimulation electrodes.

EXAMPLE 2

Patient Study

Procedure

Ten patients were enrolled. All patients were intubated with a monitored endotracheal tube (NIM Trivantage tube, Medtronic Inc). Direct laryngoscopy was performed and the larynx suspended. A bipolar probe was used to stimulate different laryngeal subsites. Bipolar stimulation was used in order to minimize current spread away from the site of stimulation. Subsites included anterior and posterior membranous vocal fold, posterior supraglottis over the medial surface of the arytenoid cartilage, mid false vocal fold, epiglottic petiole, epiglottic tip and subglottis. The maximum current approved by the IRB was 10 mA and all subsites were initially stimulated at this level and vocal fold responses recorded both visually and by the endotracheal tube electrodes. Subsites that, on 10 mA stimulation, elicited a bilateral reflex response were stimulated starting at 3 mA and increasing by 1 mA increments to define where the reflex first became bilateral. Pulse duration used was 500 uS. The study was approved by the Institutional Review Board for the Icahn School of Medicine at Mount Sinai.

Results

Ten patients were enrolled. In all patients, posterior supraglottic stimulation elicited strong bilateral contractile responses in all patients, with contractile strength increasing in an inferior to superior direction upon stimulation up the medial arytenoid cartilage. The ventricular folds and epiglottic tip elicited variable responses, most commonly ipsilateral but becoming bilateral in a subset of patients at higher currents of stimulation. Membranous vocal folds and epiglottic petiole did not elicit any reflex.

Implications for Tube Design

The presence of strong bilateral LAR responses upon stimulation posteriorly in 100% patients implies that the stimulating electrodes for the LAR tube in a preferred embodiment would be placed posteriorly, abutting the medial surface of each arytenoid cartilage. In this preferred embodiment, the recording electrodes are best placed more anteriorly, on the lateral tube surface, in order to record responses in the lateral cricoarytenoid muscles. This topography of responses with regards to the human larynx has not been previously investigated and no data except the data generated by the present Applicant exists.

EXAMPLE 3

FIG. 15 is a cross-sectional view of an exemplary electrode section of an intubation tube in accordance with the present invention. FIG. 15 lists exemplary dimensions and exemplary placements for the different types of electrodes that are part of the intubation tube. In this example, each recording electrode can have a width of about 3 mm and a length of about 30 mm. As also shown, on each side of the intubation tube, the inter-electrode gap between adjacent recording electrodes is about 7 mm. Each stimulation electrode can have a width of about 2 mm and a length of about 50 mm. As shown, the inter-electrode gap between adjacent recording electrodes can be about 4 mm. It will be appreciated that the recording electrodes in FIG. 15 can correspond to the recording electrodes 530, 540 in FIG. 13 and the stimulating electrodes can correspond to the stimulating electrodes 550 in FIG. 13.

FIGS. 10, 11 and 14 show a vocal cord level marker (cross symbol) that assists in the positioning of the device (intubation tube) relative to the vocal cord. The marker can be a line (indicia) formed on the tube for visualization.

EXAMPLE 4

Patient Study

Procedure

One hundred patients undergoing thyroidectomy (n=91) or parathyroidectomy (n=9) were included. All patients underwent pre-operative (within one month) and post-operative (within one week) laryngeal examination via flexible trans-nasal laryngoscopy. Patients with post-operative vocal fold paresis or paralysis were followed monthly until normal vocal fold function returned. Eighty patients completed Vocal Fold Handicap Index-10 questionnaires pre-operatively and one week post-operatively.

Anesthesia was induced with Propofol and succinylcholine and maintained using total intravenous anesthesia (TIVA) with Propofol and opioids (remifentanil). Inhalational and topical laryngeal anesthetic agents were avoided. Intubation was performed with a Nerve Integrity Monitor TriVantage endotracheal tube (NIM TriVantage™, Medtronics Xomed Inc.; Jacksonville, Fla., USA). The patient's neck was extended and ET position rechecked and adjusted using video laryngoscopy (GlideScope, Verathon Inc. Seattle, Wash., USA) to ensure electrodes were in direct contact with right and left laryngeal mucosa. The tube was fixed with standard tape and, in 75% of patients, an oral endotracheal tube fastener (Anchor-Fast™, Libertyville, Ill., USA).

Intraoperative Monitoring Technique

IIONM of Vagus and Recurrent Laryngeal Nerves

Nerve stimulation was performed with a monopolar handheld stimulating probe (Medtronic Xomed, Jacksonville, Fla., USA) with a subdermal sternal reference needle. Single stimuli of 0.1 ms duration with maximum intensity 2 mA at repetition rate 4 Hz were applied. Responses were stimulated and recorded on a NIM-Response 3.0 machine (Medtronic Xomed, Inc., Jacksonville, Fla., U.S.A.). Loss of signal (LOS) was defined as an EMG amplitude response below 100 µV with an absent posterior cricoarytenoid muscular twitch response on laryngeal palpation during vagal and RLN stimulation. LOS was classified into Type 1 (segmental) and Type 2 (diffuse) injury.

LAR-CIONM

The LAR was elicited by electrical stimulation of laryngeal mucosa on the side contralateral to the operative field using ET electrodes. A single-stimulus (0.1-1 ms duration) at intensity≤15 mA using the minimal current necessary for supramaximal stimulation was applied. Vocal fold adduction was recorded by ET electrodes contralateral to the stimulating side. Responses were stimulated and recorded on an Axon Sentinel 4 EP Analyzer machine (Axon Systems Inc.; Hauppauge, N.Y., U.S.A.) or Medtronic Eclipse® system (Medtronic Xomed, Inc., Jacksonville, Fla., USA). Signals were filtered (bandwidth 1.5-1,000 Hz) and stored for offline analysis.

Analysis

All patients with a decrease in vocal fold function between pre- and post-operative laryngeal examinations were analyzed. Closing LAR values were correlated with opening values, postoperative laryngeal examination findings, voice outcomes and closing CMAP values. Descriptive analyses were performed to determine the incidence of RLN paralysis. Two-tailed $P<0.05$ was considered significant. Sensitivity, specificity, and positive and negative predictive values for prediction of laryngeal functional outcome using the LAR-CIONM were calculated.

Results

In this study, the one hundred patients (134 nerves at risk) underwent neck endocrine procedures by a single surgeon (CFS) monitored continuously using LAR-CIONM in addition to IIONM. Demographics, surgical indications, surgery type and pathology are outlined in Table 3. All Bethesda 3/4 nodules underwent molecular testing prior to surgical intervention. LAR baseline values were taken prior to skin incision. If the LAR was unable to be elicited, ET position was adjusted until a reliable reflex was obtained. LAR elicitability was 100%. Mean opening and closing LAR amplitudes for patients with normal post-operative laryngeal function were 313.5±167.4 µV and 270.3±159.3 µV, respectively. By comparison, mean closing LAR amplitudes for patients with abnormal post-operative laryngeal function due to intraoperative RLN injury were significantly decreased (opening 359.1±321.0 µV, closing 93.1±47.0 µV, $p=0.04$). In every thyroid surgery transient decreases in LAR amplitude without concomitant increases in reflex latency occurred during surgical maneuvers that put traction on the RLN (FIG. 16). Releasing the tissue resulted in recovery of LAR amplitude.

TABLE 3

Patient, disease and surgical demographics
Table 1: Patient, disease and surgical demographics

| Variables | Values |
| --- | --- |
| Mean age in years (StDev) | 50.8 (15.5) |
| Gender | |
| Male | 18 |
| Female | 82 |
| Pre-operative surgical indications | |
| Goiter with compressive symptoms | 38 |
| Grave's disease | 4 |
| Bethesda 3 or 4 with high-risk molecular markers | 39 |
| Carcinoma | 10 |
| Hyperparathyroidism | 9 |
| Surgery type | |
| Left thyroid lobectomy | 31 |
| Right thyroid lobectomy | 33 |

TABLE 3-continued

Patient, disease and surgical demographics
Table 1: Patient, disease and surgical demographics

| Variables | Values |
| --- | --- |
| Total thyroidectomy | 27 |
| Parathyroidectomy | 9 |
| Pathology | |
| Benign | 53 |
| Hashimoto thyroiditis/Grave's disease | 29 |
| Malignant | 18 |
| Number of nerves at risk | 134 |
| Mean LAR-CIONM duration (minutes) | 105 |

Post-Operative Laryngeal Function in Patients with Intraoperative RLN Injury

Table 4 presents nerve injury data grouped by pre-operative nerve function. Patients 1 and 2 had normal pre-operative laryngeal examinations with post-operative hypomobility of the ipsilateral vocal fold to 50% of the contralateral fold. Both patients had palpable posterior cricoarytenoid muscle twitches during intraoperative vagal nerve stimulation. Patient 1 had a posteriorly located right 2.2 cm papillary thyroid carcinoma with extrathyroidal extension. A decrement in LAR amplitude occurred during sharp dissection of the nerve off the tumor (77.6% decrement). Normal laryngeal function returned at 5-weeks postoperatively. Patient 2 had thyromegaly with a prominent tubercle of Zuckerkandl and exhibited a 67.4% LAR amplitude decrement. She had left vocal fold hypomobility at day 3 that returned to normal by day 10 postoperatively.

Patients 3, 4 and 5 had normal pre-operative laryngeal examinations with post-operative transient vocal fold paralysis (2.2% unanticipated nerve paralysis rate). All recovered baseline laryngeal function by 6 weeks postoperatively. Patients 3 and 4 exhibited Type 2 loss of CMAP signal (LOS) presumably due to traction, and patient 5 was a Type 1 nerve injury due to heat damage from adjacent cautery. All patients had >60% amplitude decrement between the opening and closing LAR values (Table 4) and exhibited significant decreases on their VHI-10 questionnaires (mean pre-operative 0.67, mean 1-week post-operative 10.3) that returned to baseline by 6 weeks postoperatively.

Patients 6 and 7 had pre-operative vocal fold paresis with post-operative vocal fold paralysis. Both patients had posteriorly located thyroid carcinomas with features of extrathyroidal extension (ETE). For patient 6, the nerve was cut off the tumor with a Type 1 LOS at this site and a >60% amplitude decrement between the opening and closing LAR values. Final pathology showed microscopic ETE at the site of dissection. Although the vocal fold retains good tone in a medialized position, cord mobility has not returned 10 months post-operatively. Pre- and post-operative VHI-10 scores are comparable at 6.0. Patient 7 had complete encasement of the RLN by tumor and the nerve was sacrificed. A 43.1% LAR amplitude decrement occurred between opening and closing LAR values, with closing amplitude of 59.2 μV. However, opening amplitude was only 104 μV and we would thus currently classify this patient as 'not monitorable' by the LAR-CIONM technique (see discussion below). An ansa cervicalis to RLN nerve anastomosis was performed. At 5 months postoperatively, her VHI-10 score is 15, having improved from an immediate postoperative score of 20.

TABLE 4

Opening and Closing LAR values for patients with post-operative vocal fold dysfunction. Over 134 nerves at risk, 3 patients had unanticipated nerve injury resulting in postoperative vocal fold paralysis (Patients 3, 4 and 5). Patients 1 and 2 had postoperative vocal fold hypomobility (paresis) and patients 6 and 7 had direct nerve infiltration by carcinoma.

| | LAR-CIONM | | | | |
| --- | --- | --- | --- | --- | --- |
| | LatOP (ms) | LatCL (ms) | AmpOP (μV) | AmpCL (μV) | % Decrease AmpOP- AmpCL | IIONM |
| Pre-operative normal vocal fold function with post-operative paresis | | | | | | |
| Patient 1 | 17.6 | 22 | 654.3 | 146.4 | 77.6 | LTP |
| Patient 2 | 22.7 | 25.1 | 112.3 | 36.6 | 67.4 | LTP |
| Pre-operative normal vocal fold function with post-operative paralysis | | | | | | |
| Patient 3 | 28.3 | 29 | 207.5 | 80.5 | 61.2 | Type 2 LOS |
| Patient 4 | 22.4 | 23.9 | 1005.8 | 168.1 | 83.3 | Type 2 LOS |
| Patient 5 | 22.3 | 22.1 | 218 | 80 | 63.3 | Type 1 LOS |
| Pre-operative vocal fold paresis with post-operative vocal fold paralysis | | | | | | |
| Patient 6 | 19.2 | 24.3 | 419.9 | 81.1 | 80.7 | Type 1 LOS |
| Patient 7* | 25.7 | 28.3 | 104 | 59.2 | 43.1 | Transection |

AmpOP Opening LAR Amplitude, AmpCL Closing LAR Amplitude, LatOP Opening LAR Latency, LatCL Closing LAR Latency, μV microvolts, ms milliseconds, LOS loss of signal, LTP Laryngeal twitch present; * see text Defining LAR-CIONM Monitorability Criteria Of 134 nerves at risk, 5 (3.7%) were unable to be continuously monitored throughout the surgical procedure. For four of these patients (80.0%), the contralateral nerve (i.e. nerve not 'at-risk') was also unable to be monitored suggesting suboptimal stimulating electrode contact with laryngeal mucosa due to either the ET diameter being too small and/or significant secretions between tube and mucosa. These patients were successfully monitored with IIONM alone confirming that the recording electrodes were functional. For the other patient, the nerve not "at risk" was able to be monitored using the LAR, suggesting a tube rotation issue or inadequate ipsilateral mucosal contact.

For the nerve transection case and the cases of complete post-operative vocal fold paralysis, a closing LAR amplitude<100 μV was noted in 80% of cases, with no case having a closing value of zero. This residual LAR activity in cases with LOS by IIONM criteria reflects far field recordings from contraction of contralateral vocal fold musculature against ET electrodes during the bilateral reflex response. Thus, for reliable monitoring using LAR-CIONM, a minimum opening amplitude of 150 μV, optimally >200 μV, is necessary. If nerves at risk with opening amplitudes<150 μV are excluded from analysis (n=20), LAR-CIONM monitorability was 85.1%.

Defining LAR-CIONM Warning Criteria for Impending or Actual Nerve Injury

Significantly more nerves-at-risk with LAR opening-closing amplitude decrement>60% or with closing amplitude<100 μV had postoperative nerve palsies compared with nerves-at-risk without these findings (p<0.001). The positive predictive value (PPV), negative predictive value (NPV), sensitivity and specificity of the LAR-CIONM using these criteria are presented in Table 5. Of note, if patients with opening amplitudes<150 μV were excluded (n=20), there were no patients with a >60% opening-closing amplitude decrement who did not have postoperative vocal fold dysfunction and all patients with <60% decrement had normal postoperative vocal fold function. Statistically this corresponds to a PPV/NPV/sensitivity/specificity of 100%.

TABLE 5

Predictive value of irreversible LAR-CIONM amplitude decline and absolute closing value for all nerves at risk (n = 134) and excluding nerves at risk with opening amplitudes < 150 μV (n = 114).

| LAR warning criteria | Sensitivity | Specificity | PPV | NPV |
|---|---|---|---|---|
| >60% amplitude decrement | | | | |
| All patients | 85.7 (42.1-99.6) | 99.2 (95.5-100.0) | 99.2 (95.2-99.9) | 99.2 (95.2-99.9) |
| Opening amplitude < 150 μV excluded | 100.0* | 100.0* | 100.0* | 100.0* |
| Closing amplitude < 100 μV | | | | |
| All patients | 66.7 (22.3-95.7) | 98.1 (93.4-99.8) | 66.7 (31.2-89.8) | 98.1 (94.4-99.4) |
| Opening amplitude < 150 μV excluded | 66.7 (22.3-95.7) | 100.0 (96.6-100.0) | 100.0* | 98.15 (94.5-99.4) |

PPV positive predictive value, NPV negative predictive value, *see text

LAR-CIONM Complications

No patient exhibited hemodynamic instability at any time during reflex elicitation. One patient exhibited severe bradycardia (38 beats per minute) when the vagus nerve was stimulated intermittently at 1 mA without concomitant bradycardia using LAR-CIONM. There were no complications attributable directly to the monitoring technique. One patient with pre-operative cough had a worsened cough for 48 hours post-extubation and one patient with no pre-operative cough developed a cough four days after surgery that lasted for two days. One patient developed symptoms of benign positional vertigo four days postoperatively which settled with repositioning maneuvers.

Advantages of the Present Method

As discussed herein, the LAR represents a novel method to continuously monitor the vagus nerve during surgical procedures. The only commercially available vagal CIONM technique requires potentially harmful manipulation of the vagus nerve for electrode placement. Electrode dislocation intra-operatively necessitates repeat nerve manipulation and disrupts the core analysis of the Automatic Periodic Stimulation (APS®) system for detecting significant CMAP decrements. In contrast, LAR-CIONM uses non-invasive ET electrodes alone to both stimulate and record vagal responses. This methodological advantage makes the LAR-CIONM particularly attractive for minimally invasive neck surgeries and neurosurgical procedures.

LAR-CIONM Versus CMAP IONM

LAR-CIONM is exquisitely sensitive to changes in nerve excitability induced by RLN stretch or compression, necessitating frequent relaxation of tissues during surgical procedures to assess for reversibility of observed LAR-CIONM amplitude decrements. LAR-CIONM can thus provide very early warning of potential nerve injury and may prove more effective than CMAP responses in preventing type 2 LOS injuries because traction injuries are reversible when prompt corrective measures are applied. Increased latency of LAR responses did not predict nerve injury in this series. This suggests that the concept of the 'combined event' to predict postoperative nerve paralysis for CMAP responses may not apply to the LAR. It is recognized that trial-to-trial, a reflex is physiologically conducted by different axon fibers with varying conduction velocities which may contribute to latency variability during LAR-CIONM. Also, slight movements of the tube relative to the mucosa during surgical tissue manipulation may intermittently favor cathodic or anodic axonal depolarization, thereby increasing LAR latency variability.

Monitoring LAR Using Ipsilateral Responses of the LAR

In yet another aspect of the present invention, the devices and method disclosed herein can be adapted to monitor the LAR using the ipsilateral iR1 component of the reflex for both stimulation and recording purposes.

Surface electrodes ipsilateral to the surgical field (and also ipsilateral to the stimulation side) attached to the endotracheal tube can be used to record the ipsilateral R1 (iR1) and R2 (iR2) responses of the LAR. The iR1 and iR2 responses were defined as the short and long-latency responses, respectively, elicited in the ipsilateral vocal fold muscles relative to the stimulating side. For example, the device shown in FIG. 13 can be adapted and configured such that posterior pair of electrodes 550 act as the stimulating electrodes and due to their posterior position, these electrodes 550 will elicit an ipsilateral response that is recoded by an ipsilateral recording electrode, such as electrode(s) 530 and/or 540. In yet another electrode arrangement, the device of FIG. 13 can be modified such that that the stimulating electrodes 550 can be eliminated or rendered inactive and for each of the pairs of electrodes 530, 540, the posterior electrode of the pair acts as a stimulating electrode, while the anterior electrode of the pair acts as the recording electrode. In this manner, the recording and stimulating electrodes are located on the same side of the tube. Ipsilateral iR1 recording can be achieved by separation of the stimulation electrode(s) from the recording electrode(s) with the stimulation electrode(s) being placed posterior to the recording electrode(s). It will be understood that these teachings can also be implemented in tubes having other constructions such as the other ones described herein.

Monitoring both sensory and motor pathways of the laryngeal nerves during neck surgery can be accomplished by eliciting the LAR in patients under total intravenous general anesthesia. This novel methodology is simple, non-invasive and widely applicable as it uses a commercially available endotracheal tube for stimulating laryngeal mucosa on one side and recording ipsilateral vocal fold responses on the same side (iR1 and iR2).

It will be understood that the foregoing dimensions are only exemplary in nature and therefore are not limiting of the present invention. The size of the electrodes and the relative placements thereof can therefore differ from the foregoing example.

It is to be understood that like numerals in the drawings represent like elements through the several figures, and that not all components and/or steps described and illustrated with reference to the figures are required for all embodiments or arrangements.

The subject matter described above is provided by way of illustration only and should not be construed as limiting. Various modifications and changes can be made to the subject matter described herein without following the example embodiments and applications illustrated and described, and without departing from the true spirit and scope of the present disclosure, which is set forth in the following claims.

What is claimed is:

1. A method for intraoperatively monitoring laryngeal and vagus nerves comprising the step of:
eliciting laryngeal adductor response (LAR) in a patient that is under general anesthesia, that is of a type that preserves LAR, by applying electrical stimulation to the laryngeal supraglottic mucosa using endotracheal tube surface based electrodes and by monitoring contralateral responses of the LAR that are detected after application of electrical stimulation using the endotracheal tube surface based electrodes.

2. The method of claim 1, wherein the step of eliciting the LAR comprises the step of electrically stimulating the laryngeal supraglottic mucosa on a side contralateral to an operative field using a right surface electrode or left surface electrode associated with an outer surface of the endotracheal tube.

3. The method of claim 1, furthering comprising the step of positioning the endotracheal tube surface based electrodes in direct contact with right and left vocal folds.

4. The method of claim 1, wherein at least one of the endotracheal tube surface based electrodes is configured to emit the electrical stimulation and at least one other of the surface based electrodes is configured to record the contralateral responses of the LAR.

5. The method of claim 4, wherein the contralateral responses comprises contralateral R1 (cR1) and R2 (cR2) responses of the LAR.

6. The method of claim 1, wherein the endotracheal tube comprises a first inflatable member and an electrode area that is proximal to the first inflatable member and includes the endotracheal tube surface based electrodes, wherein at least one of the endotracheal tube surface based electrodes is configured to emit the electrical stimulation and at least one other endotracheal tube surface based electrode is configured to record the contralateral responses of the LAR.

7. The method of claim 6, wherein at least one electrode on one side of the endotracheal tube and at least one electrode on the other side of the endotracheal tube are each configured to both emit electrical stimulation and record the contralateral responses of the LAR.

8. The method of claim 6, wherein the at least one of the endotracheal tube surface based electrodes comprises a first array of electrodes and the at least one other endotracheal tube surface based electrode comprises a second array of electrodes.

9. The method of claim 6, wherein the electrode area of the endotracheal tube has a generally triangular shaped cross-sectional portion that extends radially outward from a circular shaped portion of the endotracheal tube and is configured for mating with a larynx anatomy of the patient.

10. The method of claim 9, wherein the generally triangular shaped cross-section is defined by a first side wall and an opposing second side wall, the first side wall including a first array of surface based electrodes and the second side wall including a second array of surface based electrodes.

11. The method of claim 10, further including a second inflatable member for placement distal to a larynx of the patient and wherein the endotracheal tube surface based electrodes are disposed between the first and second inflatable members.

12. The method of claim 11, wherein each of the first and second inflatable members comprises an inflatable cuff or balloon.

13. The method of claim 11, wherein endotracheal tube surface based electrodes disposed between the first and second inflatable members comprise bi-lateral electrode arrays.

14. The method of claim 11, wherein the second inflatable member includes at least one stimulation electrode for providing the electrical stimulation and the endotracheal tube surface based electrodes disposed between the first and second inflatable members comprise electrodes that only record contralateral responses of the LAR.

15. The method of claim 14, wherein the at least one stimulation electrode enables continuous intra-operative neuromonitoring CIONM without use of a vagal electrode.

16. The method of claim 1, wherein monitoring the laryngeal and vagus nerves includes monitoring the superior laryngeal nerve (iSLN).

17. The method of claim 10, wherein the electrical stimulation is provided by a stimulation electrode that is associated with a second inflatable member that is positioned distal to the larynx of the patient.

18. The method of claim 1, wherein the general anesthesia comprises total intravenous anesthesia (TIVA).

19. A system for intraoperatively monitoring laryngeal and vagus nerves by eliciting laryngeal adductor response (LAR) in a patient that is under general anesthesia, that is of a type that preserves LAR, and by monitoring responses of the LAR that are detected after application of electrical stimulation to the laryngeal supraglottic mucosa comprising:
an endotracheal tube having a first inflatable member and electrode area that includes a plurality of surface based electrodes, wherein the surface based electrodes includes a first surface based electrode that is located along a first side of the endotracheal tube and a second surface based electrode that is located along a second side the endotracheal tube, each of the first and second surface based electrodes being configured to emit electrical stimulation to the laryngeal supraglottic mucosa and record the responses of the LAR; and
a signal generator/receiver that is electrically coupled to the surface based electrodes and is configured to deliver electrical stimulation to a selected one of the first and second surface based electrodes and record the responses of the LAR from the other of the first and second surface based electrodes.

20. The system of claim 19, wherein the surface based electrodes are configured for positioning in direct contact with right and left vocal folds.

21. The system of claim 19, wherein the responses comprises R1 and R2 responses of the LAR.

22. The system of claim 19, wherein the first surface based electrode comprises a first array of electrodes and the second surface based electrode comprises a second array of electrodes.

23. The system of claim 22, where the first array of electrodes comprises a plurality of parallel spaced electrodes that are electrically interconnected and the second array of electrodes comprises a plurality of parallel spaced electrodes that are electrically interconnected.

24. The system of claim 19, wherein the electrode area of the endotracheal tube has a generally triangular shaped cross-section configured for mating with a larynx anatomy of the patient.

25. The system of claim 24, wherein the generally triangular shaped cross-section is defined by a first side wall and an opposing second side wall, the first side wall including the first surface based electrode which comprises a first array of surface based electrodes and the second side wall including the second surface based electrode which comprises a second array of surface based electrodes.

26. The system of claim 19, further including a second inflatable member for placement distal to a larynx of the patient and wherein the endotracheal tube surface based electrodes are disposed between the first and second inflatable members.

27. The system of claim 26, wherein each of the first and second inflatable members comprises an inflatable cuff or balloon.

28. The system of claim 26, wherein surface based electrodes disposed between the first and second inflatable members comprise bi-lateral electrode arrays.

29. The system of claim 26, wherein the second inflatable member includes at least one stimulation electrode for providing the electrical stimulation and the surface based electrodes disposed between the first and second inflatable members comprise electrodes that only record responses of the LAR.

30. The system of claim 29, wherein the at least one stimulation electrode enables CIONM without use of a vagal electrode.

31. The system of claim 19, wherein the surface based electrodes are electrically connected to the signal generator/receiver by means of wires.

32. An endotracheal tube for intraoperatively monitoring laryngeal and vagus nerves by eliciting laryngeal adductor response (LAR) in a patient that is under general anesthesia, that is of a type that preserves LAR, and by monitoring contralateral responses of the LAR that are detected after application of electrical stimulation to the laryngeal supraglottic mucosa comprising:
an endotracheal tube body having a first inflatable member and electrode area that has a generally triangular shaped cross-section configured for mating with a larynx anatomy of the patient, the electrode area including a plurality of surface based electrodes, wherein the surface based electrodes includes a first surface based electrode that is located along a first side of the endotracheal tube and a second surface based electrode that is located along a second side the endotracheal tube, each of the first and second surface based electrodes being configured to emit electrical stimulation to the laryngeal supraglottic mucosa and record the contralateral responses of the LAR.

33. The endotracheal tube of claim 32, further including a second inflatable member for placement distal to a larynx of the patient and wherein the endotracheal tube surface based electrodes are disposed between the first and second inflatable members.

34. The endotracheal tube of claim 33, wherein each of the first and second inflatable members comprises an inflatable cuff or balloon.

35. The endotracheal tube of claim 33, wherein surface based electrodes disposed between the first and second inflatable members comprise bi-lateral electrode arrays.

36. An endotracheal tube for intraoperatively monitoring laryngeal and vagus nerves by eliciting laryngeal adductor response (LAR) in a patient that is under general anesthesia, that is of a type that preserves LAR, and by monitoring contralateral responses of the LAR that are detected after application of electrical stimulation to the laryngeal supraglottic mucosa comprising:
an endotracheal tube body having a first inflatable member and electrode area that has a generally triangular shaped cross-section configured for mating with a larynx anatomy of the patient, the electrode area including a plurality of surface based electrodes, wherein the surface based electrodes includes a first surface based electrode that is located along a first side of the endotracheal tube and a second surface based electrode that is located along a second side the endotracheal tube, each of the first and second surface based electrodes being configured to record the contralateral responses of the LAR;
a second inflatable member for placement distal to a larynx of the patient and wherein the endotracheal tube surface based electrodes are disposed between the first and second inflatable members; and
wherein the second inflatable member includes at least one stimulation electrode for providing the electrical stimulation to the laryngeal supraglottic mucosa and the surface based electrodes disposed between the first and second inflatable members comprise electrodes that only record contralateral responses of the LAR.

37. The endotracheal tube of claim 36, wherein the at least one stimulation electrode enables continuous intra-operative neuromonitoring (CIONM) without use of a vagal electrode.

38. An endotracheal tube for intraoperatively monitoring laryngeal and vagus nerves by eliciting laryngeal adductor response (LAR) in a patient that is under general anesthesia, that is of a type that preserves LAR, and by monitoring responses of the LAR that are detected after application of electrical stimulation to the laryngeal supraglottic mucosa comprising:
an endotracheal tube body having a first inflatable member and an electrode area configured for mating with a larynx anatomy of the patient, the electrode area of the endotracheal tube including a first surface section having a first plurality of surface based recording electrodes, a second surface section having a second plurality of surface based electrodes and a third surface section having a stimulation electrode, wherein the first and second pluralities of surface based recording electrodes being configured to record responses of the LAR, the stimulation electrode being configured to emit electrical stimulation to the laryngeal supraglottic mucosa.

39. The endotracheal tube of claim 38, wherein the electrode area is defined by a posterior portion and an anterior portion, the posterior portion having a generally circular shape and the anterior portion comprising a protrusion that extends radially outward from the posterior portion.

40. The endotracheal tube of claim 38, wherein the first plurality of surface based recording electrodes comprise a pair of electrodes that are located along the first surface section of the endotracheal tube and the at least one second surface based recording electrode comprises a pair of electrodes that are located along the second side the endotracheal tube, wherein the stimulation electrode is located between the pair of first surface based recording electrodes and the pair of second surface based recording electrodes.

41. The endotracheal tube of claim 40, wherein the first surface based recording electrodes, the second surface based recording electrodes, and the stimulation electrode extend in a longitudinal direction along the outer surface of the endotracheal tube.

42. The endotracheal tube of claim 38, wherein there are a pair of stimulation electrodes.

43. The endotracheal tube of claim 38, wherein the stimulation electrode is located along a posterior side of the electrode area between the first surface section along which the first plurality of surface based recording electrodes are located and the second surface section along which the second plurality of surface based recording electrodes are located.

44. The endotracheal tube of claim 43, wherein the stimulation electrode comprises a pair of stimulation electrodes that are spaced apart and are parallel to one another, the first plurality of surface based recording electrodes being spaced apart and parallel to one another and the second plurality of surface based recording electrodes being spaced apart and parallel to one another.

45. The endotracheal tube of claim 38, wherein the stimulation electrode enables continuous intra-operative neuromonitoring (CIONM) without use of a vagal electrode.

46. The endotracheal tube of claim 38, further including a first inflatable member and a second inflatable member with the electrode area being between the first and second inflatable members, the second inflatable member located for placement distal to a larynx of the patient.

47. An endotracheal tube for intraoperatively monitoring laryngeal and vagus nerves by eliciting laryngeal adductor response (LAR) in a patient that is under general anesthesia, that is of a type that preserves LAR, and by monitoring ipsilateral responses of the LAR that are detected after application of electrical stimulation to the laryngeal supraglottic mucosa comprising:

an endotracheal tube body having a first inflatable member and electrode area that has a generally triangular shaped cross-section configured for mating with a larynx anatomy of the patient, the electrode area including a plurality of surface based electrodes, wherein the surface based electrodes includes a first surface based electrode that is located along a first side of the endotracheal tube and a second surface based electrode that is located along a second side the endotracheal tube, and a first stimulation electrode located posterior to the first surface based electrode along the first side and a second stimulation electrode located posterior to the second surface based electrode along the second side, the first surface based electrode recording the ipsilateral responses of the LAR in response to activation of the first stimulating electrode and stimulation of the laryngeal supraglottic mucosa and the second surface based electrode recording the ipsilateral responses of the LAR in response to activation of the second stimulating electrode and stimulation of the laryngeal supraglottic mucosa.

* * * * *